US006686330B2

(12) United States Patent
Jordan, IV et al.

(10) Patent No.: US 6,686,330 B2
(45) Date of Patent: Feb. 3, 2004

(54) COMPOSITIONS INCLUDING ETHER-CAPPED POLY (OXYALKYLATED) ALCOHOL WETTING AGENTS

(75) Inventors: Glenn Thomas Jordan, IV, Indian Springs, OH (US); William Michael Scheper, Lawrenceburg, IN (US); Mark Robert Sivik, Mason, OH (US); Bernard William Kluesener, Harrison, OH (US); Kristen Lynne McKenzie, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 384 days.

(21) Appl. No.: 09/733,450

(22) Filed: Dec. 8, 2000

(65) Prior Publication Data

US 2002/0058601 A1 May 16, 2002

Related U.S. Application Data

(63) Continuation-in-part of application No. 09/659,895, filed on Sep. 12, 2000, and a continuation-in-part of application No. 09/663,576, filed on Sep. 12, 2000.

(60) Provisional application No. 60/232,298, filed on Sep. 12, 2000, provisional application No. 60/178,877, filed on Jan. 28, 2000, provisional application No. 60/178,803, filed on Jan. 28, 2000, provisional application No. 60/169,632, filed on Dec. 8, 1999, and provisional application No. 60/169,585, filed on Dec. 8, 1999.

(51) Int. Cl.[7] ............................. C11D 1/72; C11D 1/722
(52) U.S. Cl. .................. 510/475; 510/356; 510/360; 510/413; 510/421; 510/535
(58) Field of Search ................................ 510/356, 413, 510/421, 475, 535, 360

(56) References Cited

U.S. PATENT DOCUMENTS

| | | |
|---|---|---|
| 3,082,172 A | 3/1963 | Temple et al. |
| 3,255,117 A | 6/1966 | Knapp et al. |
| 3,281,475 A | 10/1966 | Boettner et al. |
| 4,272,394 A | 6/1981 | Kaneko |
| 4,317,940 A | 3/1982 | Scardera et al. |
| 4,827,028 A | 5/1989 | Scardera et al. |
| 4,898,621 A | 2/1990 | Pruehs et al. |
| 4,902,834 A | 2/1990 | Otten et al. |
| 4,913,833 A | 4/1990 | Otten et al. |
| 4,925,587 A | 5/1990 | Schenker et al. |
| 5,073,286 A | 12/1991 | Otten et al. |
| 5,206,443 A | 4/1993 | Baur et al. |
| 5,294,365 A | 3/1994 | Welch et al. |
| 5,346,973 A | 9/1994 | Feustel et al. |
| 5,425,894 A | 6/1995 | Welch et al. |
| 5,576,281 A | 11/1996 | Bunch et al. |
| 5,677,273 A | 10/1997 | Schmid et al. |
| 5,921,910 A | 7/1999 | Schmid et al. |

FOREIGN PATENT DOCUMENTS

| | | | |
|---|---|---|---|
| DE | 2252186 A | 5/1974 | |
| DE | 2556544 A | 6/1977 | |
| EP | 0337760 A | 10/1989 | |
| EP | 0638635 A1 | 2/1995 | |
| EP | WO 95/13260 * | 5/1995 | ......... C07C/43/315 |
| EP | 0675942 B1 | 7/1997 | |
| GB | 2158080 A | 11/1985 | |
| WO | WO 93/04153 A1 | 3/1993 | |
| WO | WO 94/22800 A1 | 10/1994 | |
| WO | WO 95/13260 A1 | 5/1995 | |
| WO | WO 96/00253 A | 1/1996 | |
| WO | WO 96/12001 A1 | 4/1996 | |
| WO | WO 98/17379 A1 | 4/1998 | |
| WO | WO 99/06466 A1 | 2/1999 | |

* cited by examiner

Primary Examiner—Brian P Mruk
(74) Attorney, Agent, or Firm—Kim W. Zerby; Steven W. Miller

(57) ABSTRACT

Compositions including ether-capped poly(oxyalkylated) alcohol wetting agents. The wetting agents are low-foaming and have good biodegradability, and can be used in a variety of applications, for example in polymer, anti-foaming, biocidal, coating, fertilizer, pharmaceutical, and drilling fluid compositions.

28 Claims, No Drawings

COMPOSITIONS INCLUDING ETHER-CAPPED POLY (OXYALKYLATED) ALCOHOL WETTING AGENTS

RELATED APPLICATIONS

This application is a continuation-in-part which claims priority to U.S. Provisional Application No. 60/232,298, filed on Sep. 12, 2000; U.S. application Ser. No. 09/659,895, filed on Sep. 12, 2000, which claims priority to U.S. Provisional Application No. 60/169.632, filed on Dec. 8, 1999; U.S. Provisional Application No. 60/178,877, filed Jan. 28, 2000; and U.S. application Ser. No. 09/663,576, filed Sep. 12, 2000, which claims priority to U.S. Provisional Application No. 60/169,585, filed Dec. 8, 1999, U.S. Provisional Application No. 60/178,803, filed Jan. 28, 2000.

TECHNICAL FIELD

The present invention relates to compositions containing low-foaming nonionic wetting agents.

BACKGROUND OF THE INVENTION

Due to the varied nature of different compositions, different wetting agents are better suited for some applications while being less suited or totally unsuitable for other applications. While some wetting agents provide the desired properties, such as dispersion or suspension of other ingredients, they are high foaming or not readily biodegradable. Conversely, a wetting agent may be suitably low foaming, but provide less that suitable dispersion or suspension of other ingredients.

Accordingly, the need remains for new wetting agents which are suitable for use in a variety of compositions and applications that can provide improve dissolution, improved rates of mixing with water, improved streaking and filming performance, good wetting, adequate dispersion and/or suspension, suds control and good biodegradability, while avoiding incompatibility with other components of the compositions.

SUMMARY OF THE INVENTION

In accordance with a first aspect of the present invention, a composition comprising an ether-capped poly (oxyalkylated) alcohol wetting agent is provided. The composition comprises:

(a) from about 0.01% to about 50%, preferably from about 0.1% to about 20%, more preferably from about 0.1% to about 10%, by weight of the composition of a wetting agent, wherein said wetting agent comprises an ether-capped poly(oxyalkylated) alcohol having the formula:

$$RO(R^1O)_xCH(CH_3)OR^2$$

wherein R is selected from the group consisting of linear or branched, saturated or unsaturated, substituted or unsubstituted, aliphatic or aromatic hydrocarbon radicals having from about 1 to about 30 carbon atoms; $R^1$ may be the same or different, and is independently selected from the group consisting of branched or linear $C_2$ to $C_7$ alkylene in any given molecule; x is a number from 1 to about 30; and $R^2$ is selected from the group consisting of:

(i) a 4 to 8 membered substituted, or unsubstituted heterocyclic ring containing from 1 to 3 hetero atoms; and
(ii) linear or branched, saturated or unsaturated, substituted or unsubstituted, cyclic or acyclic, aliphatic or aromatic hydrocarbon radicals having from about 1 to about 30 carbon atoms;

provided that when $R^2$ is (ii) then either at least one of $R^1$ is other than $C_2$ to $C_3$ alkylene or $R^2$ has from 6 to 30 carbon atoms; and (b) from about 0.1% to about 99% by weight of the composition of an adjunct ingredient.

These and other aspects, features and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

Once again, the first aspect of the present invention is directed toward compositions comprising low-foaming nonionic wetting agents. The wetting agents of the present invention are of the formula:

$$RO(R^1O)_xCH(CH_3)OR^2$$

In one aspect of the present invention, R is a linear or branched, saturated or unsaturated, substituted or unsubstituted, aliphatic hydrocarbon radical having from about 1 to about 20 carbon atoms. Even more preferably R is a linear or branched, saturated, aliphatic hydrocarbon radical having from about 4 to about 18, preferably from about 8 to about 16, carbon atoms.

In one aspect of the present invention R, $R^1$ and $R^2$ are selected such that the ether-capped poly(oxyalkylated) alcohol contains one or more chiral carbon atoms.

In one aspect of the present invention the ether-capped poly(oxyalkylated) alcohol is a mixture of ether-capped poly(oxyalkylated) alcohols. This mixture can be obtained in a variety of ways, for example, by mixing two ether-capped poly(oxyalkylated) alcohols together, or by forming the ether-capped poly(oxyalkylated) alcohols from a mixture of alcohols, in which the reaction used to produce the ether-capped poly(oxyalkylated) alcohols forms a racemic mixture, or by alkoxylating under conditions such that the ether-capped poly(oxyalkylated) alcohol produced is a mixture with a range of different alkoxy groups present on each ether-capped poly(oxyalkylated) alcohol. These example are intended to be illustrative, and in no way limiting in the scope of the invention.

In one aspect of the present invention, R is a hydrocarbon radical of the formula:

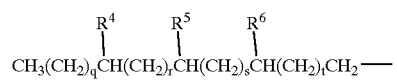

wherein $R^4$, $R^5$, and $R^6$ are each independently selected from hydrogen and $C_1$–$C_3$ alkyl, more preferably hydrogen and $C_1$–$C_2$ alkyl, even more preferably hydrogen and methyl, provided that $R^4$, $R^5$, and $R^6$ are not all hydrogen and, when t is 0, at least $R^4$ or $R^5$ is not hydrogen; q, r, s, and t are each independently integers from 0 to 13. In one more preferred form of this aspect R is selected from the formulas:

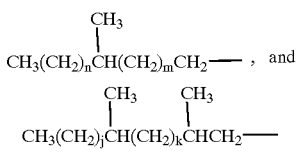

wherein n, m, j and k are each independently integers from 0 to 13.

In one aspect of the present invention $R^2$ is a hydrocarbon radical of the formula:

—C(CH$_3$)$_2$R$^3$ wherein $R^3$ is selected from the group consisting of linear or branched, saturated or unsaturated, substituted or unsubstituted, aliphatic or aromatic hydrocarbon radicals having from about 1 to about 30, more preferably 1 to 20, even more preferably 1 to 15, carbon atoms. In one embodiment of this aspect of the present invention, $R^3$ is —CH$_2$CH$_3$.

In the novel compounds of the present invention, when $R^2$ is (ii) then either at least one of $R^1$ is other than $C_2$ to $C_3$ alkylene or $R^2$ has from 6 to 30 carbon atoms. That is, when $R^2$ is (ii) $R^2$ is either a linear or branched, saturated or unsaturated, substituted or unsubstituted, aliphatic or aromatic hydrocarbon radical having from about 6 to about 30 carbon atoms or a linear or branched, saturated or unsaturated, substituted or unsubstituted, aliphatic or aromatic hydrocarbon radical having from about 1 to about 30 carbon atoms, with at least one of $R^1$ being other than $C_2$ to $C_3$ alkylene. For example, when $R^2$ is a hydrocarbon of the formula:

—(CH$_2$)$_y$—X where y and X are described hereafter, or $R^2$ is a hydrocarbon radical of the formula:

C(CH$_3$)$_2$R$^3$ where $R^3$ is hereinbefore described, then at least one of $R^1$ is other than $C_2$ to $C_3$ alkylene. For example, if x is 5, and $R^2$ is (CH$_2$)$_y$—X, then the ether-capped poly (oxyalkylated) alcohol could have the formula:

RO(CH$_2$CH(CH$_2$CH$_3$)O)$_5$CH(CH$_3$)O—(CH$_2$)$_y$—X or

RO(CH$_2$CH$_2$O)$_4$(CH$_2$CH(CH$_2$CH$_3$)O)CH(CH$_3$)O—(CH$_2$)$_y$—X or

RO(CH$_2$CHCH$_3$O)(CH$_2$CH(CH$_2$CH$_3$)O)$_4$CH(CH$_3$)O—(CH$_2$)$_y$—X

Similarly, for example if $R^2$ is —C(CH$_3$)$_2$R$^3$ and x is 7, then the ether-capped poly(oxyalkylated) alcohol could have the formula:

RO(CH$_2$CH$_2$O)$_6$(CH$_2$CH$_2$(CH$_2$CH$_3$)O)CH(CH$_3$)O—C(CH$_3$)$_2$R$^3$ or

RO(CH$_2$CHCH$_3$O)$_4$(CH$_2$CH(CH$_2$CH$_3$)O)$_3$CH(CH$_3$)O—C(CH$_3$)$_2$R$^3$ or

RO(CH$_2$CH$_2$O)$_3$(CH$_2$CHCH$_3$O)$_2$(CH$_2$CH(CH$_2$CH$_3$)O)(CH$_2$CH(CH$_2$CH$_3$CH)O)CH(CH$_3$)O—C(CH$_3$)$_2$R$^3$

These above examples are included merely for illustrative purposes and are not to be construed in any manner as limiting of the scope of the present invention.

In one aspect of the present invention $R^2$ is a 4 to 8 membered substituted or unsubstituted heterocyclic ring containing from 1 to 3 heteroatoms. In one embodiment of this aspect of the invention the heteroatoms are selected from the group comprising oxygen, nitrogen, sulfur and mixtures thereof. In one embodiment of this aspect of the invention $R^2$ is a 5 or 6 member heterocycle. In another embodiment of this aspect of the present invention $R^2$ is selected from the group consisting of:

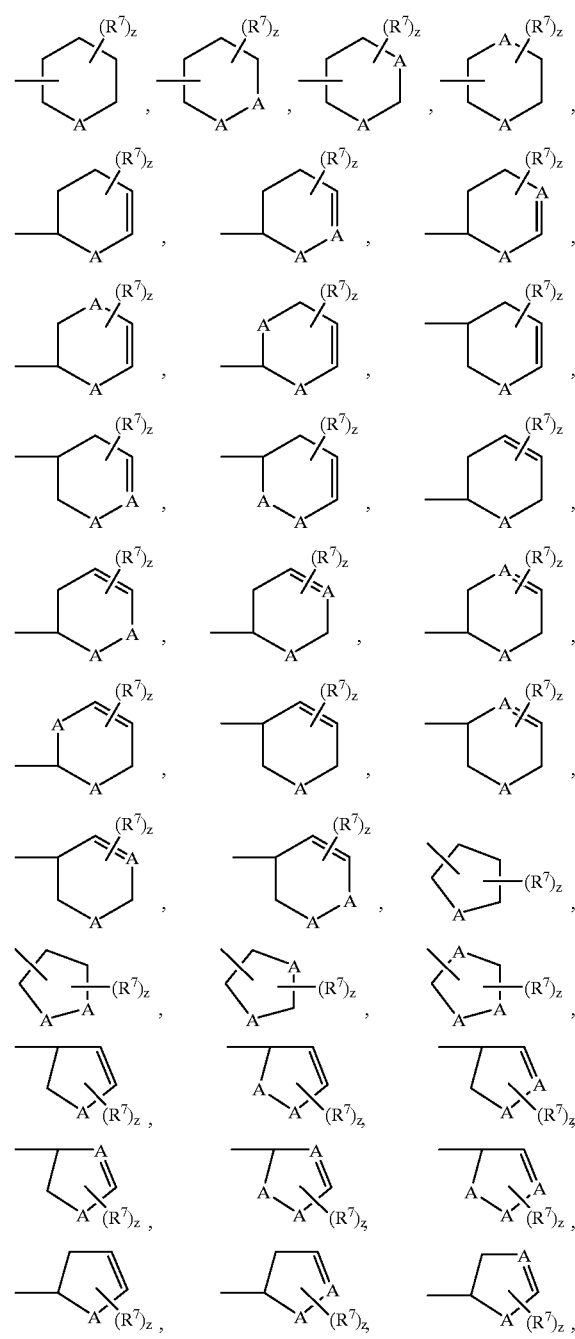

-continued

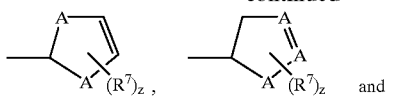

wherein each $R^7$ is independently selected from the group consisting of hydrogen and linear or branched, saturated or unsaturated, substituted or unsubstituted, aliphatic hydrocarbon or alkoxy radicals having from about 1 to about 10 carbon atoms, or $R^7$ is a saturated or unsaturated, substituted or unsubstituted, alicyclic or aromatic hydrocarbon radical having from about 1 to about 10 carbon atoms, which is fused to the heterocyclic ring; each A is independently selected from the group consisting of O, and $N(R^8)_a$, wherein $R^8$ is independently selected from the group consisting of hydrogen and linear or branched, saturated or unsaturated, substituted or unsubstituted, aliphatic hydrocarbon radicals having from about 1 to about 10 carbon atoms, and a is either 0 or 1; and z is an integer from 1 to 3.

In another embodiment of this aspect of the present invention $R^2$ is selected from the group consisting of:

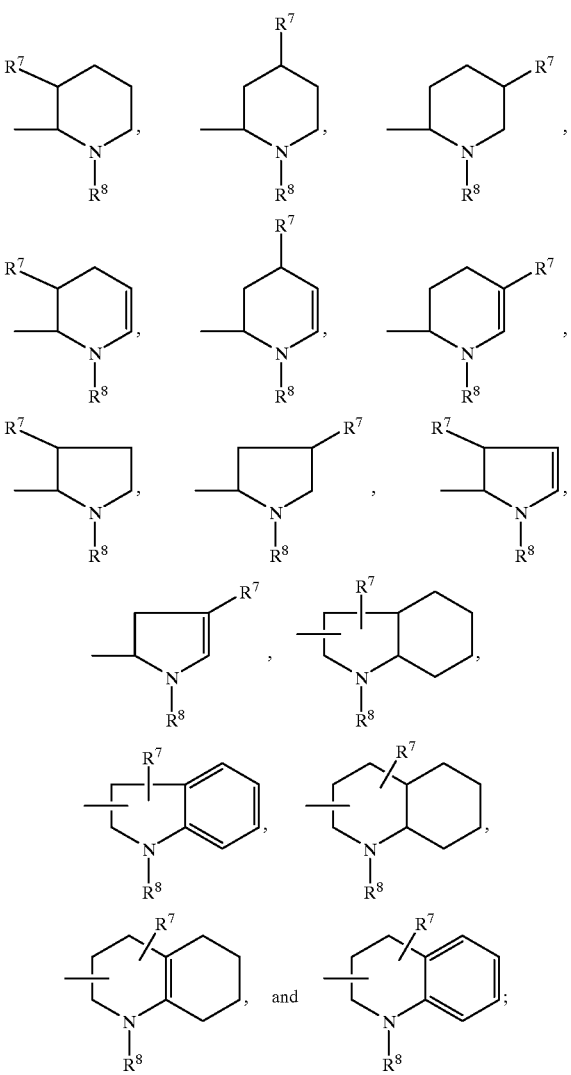

wherein $R^7$ is defined as above. Preferably, the above ether-capped poly(oxyalkylated) alcohol contains a chiral center.

In another embodiment of this aspect of the present invention $R^2$ is selected from the group consisting of:

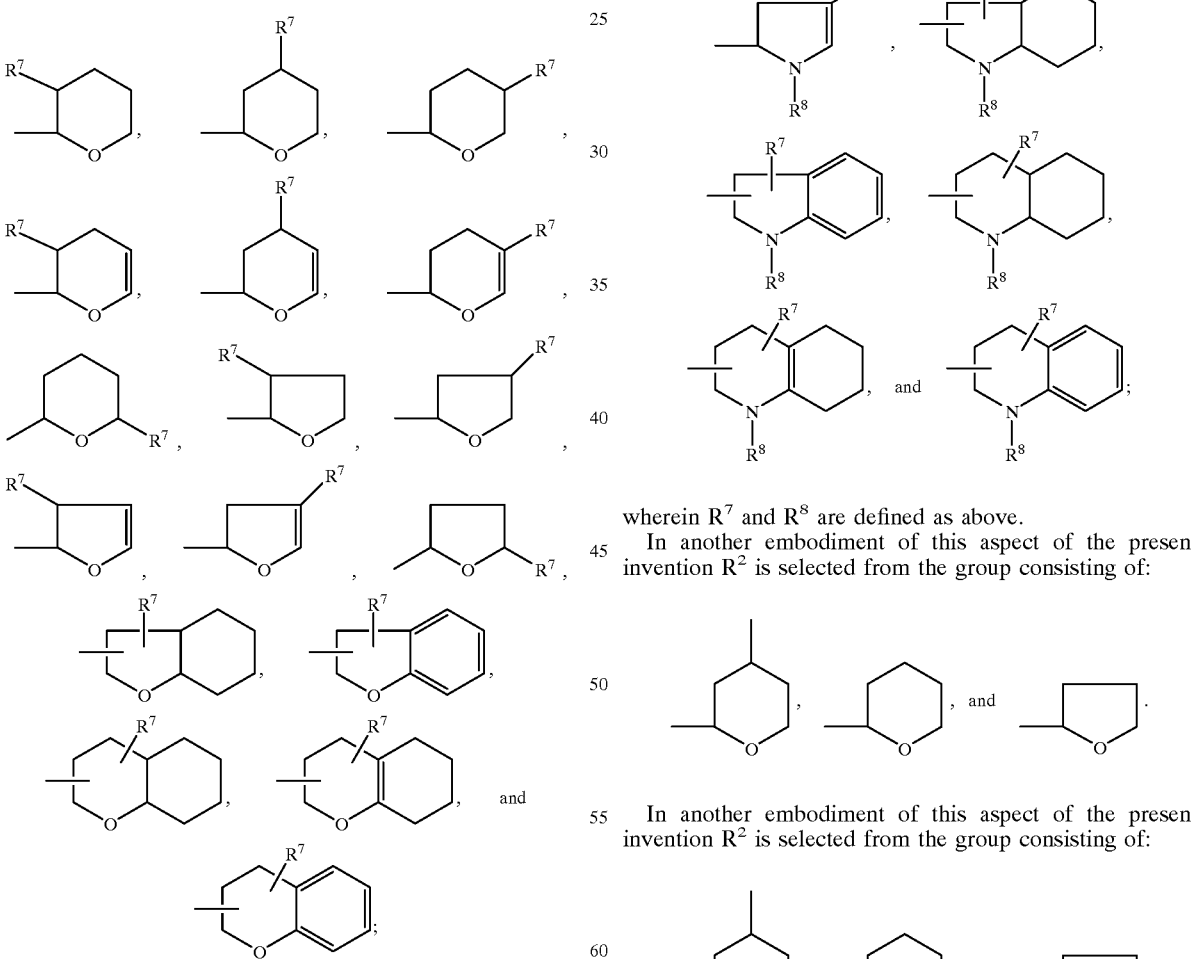

wherein $R^7$ and $R^8$ are defined as above.

In another embodiment of this aspect of the present invention $R^2$ is selected from the group consisting of:

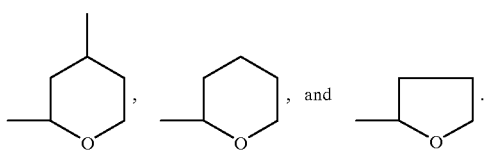

In another embodiment of this aspect of the present invention $R^2$ is selected from the group consisting of:

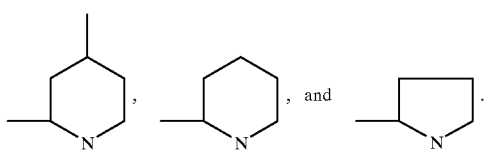

In one aspect of the present invention $R^2$ is a 7 to 13 membered substituted, or unsubstituted polycyclic ring. In one embodiment of this aspect of the present invention $R^2$ is selected from the group consisting of substituted or unsubstituted adamantane, substituted or unsubstituted norbornane, substituted or unsubstituted nortricyclene, and substituted or unsubstituted bicyclo[2.2.2]octane. In another embodiment of this aspect of the present invention $R^2$ is a substituted or unsubstituted adamantane.

In one embodiment of the invention, R is selected from the group consisting of linear or branched, aliphatic hydrocarbon radicals having from about 7 to about 11 carbon atoms; x is a number from 6 to about 10; and $R^2$ is selected from the group consisting of a hydrocarbon radical of the formula:

wherein $R^3$ is selected from the group consisting of linear or branched, aliphatic radicals having from about 2 to about 5 carbon atoms.

In one aspect of the present invention $R^2$ is a hydrocarbon of the formula:

wherein y is an integer from 0 to 7, X is a 4 to 8, preferably 5 or 6, membered substituted or unsubstituted, saturated or unsaturated, cyclic or aromatic hydrocarbon radical. In another embodiment of this aspect of the present invention y is an integer from 1 to 2, and X is selected from the group consisting of 5 to 8 membered substituted or unsubstituted, aromatic hydrocarbon radicals.

In another embodiment of this aspect of the present invention y is 0 and X is a 5 or 6 membered substituted or unsubstituted, saturated or unsaturated, cyclic or aromatic hydrocarbon radical.

In another embodiment of this aspect of the present invention X is selected from the group consisting of:

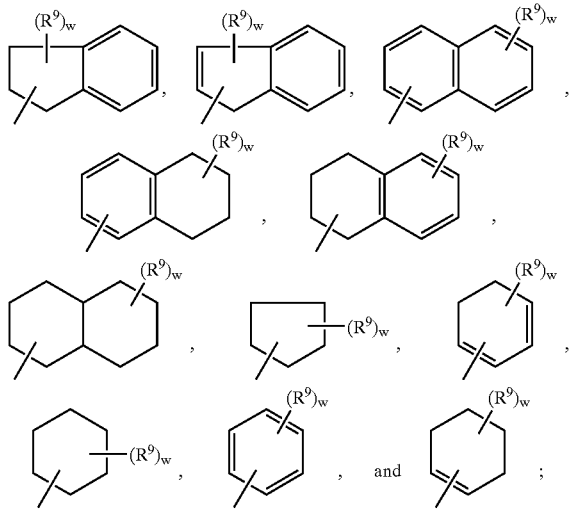

wherein each $R^9$ is independently selected from the group consisting of hydrogen, linear or branched, saturated or unsaturated, substituted or unsubstituted, aliphatic hydrocarbon or alkoxy radicals having from about 1 to about 10 carbon atoms, or each $R^9$ is a saturated or unsaturated, substituted or unsubstituted, alicyclic or aromatic hydrocarbon radical having from about 1 to about 10 carbon atoms, which is fused to the ring; and w is an integer from 1 to 3.

In another embodiment of this aspect of the present invention X is selected from the group consisting of:

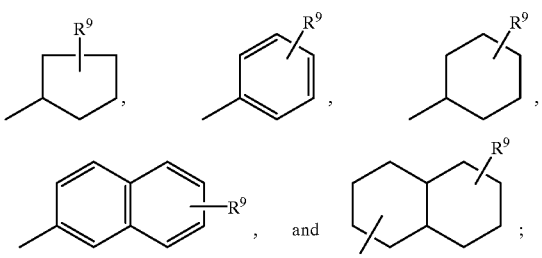

wherein each $R^9$ is defined as above.

In another embodiment of this aspect of the present invention X is selected from the group consisting of:

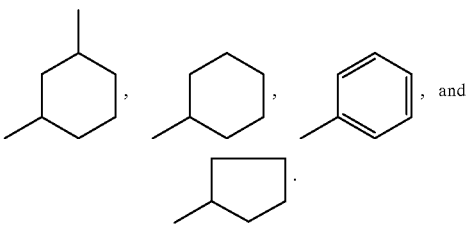

In one aspect of the present invention $R^2$ is a linear or branched, saturated or unsaturated, substituted or unsubstituted, aliphatic or aromatic hydrocarbon radical having from about 1 to about 30 carbon atoms, more preferably $R^2$ is a linear or branched, saturated or unsaturated, substituted or unsubstituted, aliphatic hydrocarbon radical having from about 1 to about 20 carbon atoms, even more preferably $R^2$ is a linear or branched, saturated, aliphatic hydrocarbon radicals having from about 4 to about 18, preferably from about 8 to about 16, carbon atoms.

In one aspect of the present invention, when x is greater than 2, $R^1$ may be the same or different. That is, $R^1$ may vary between any of the $C_2$ to $C_7$ alkylene units as described above. For instance, if x is 3, $R^1$ may be selected to form ethyleneoxy (EO) or propyleneoxy (PO) and may vary in order of (EO)(PO)(EO), (EO)(EO)(PO); (EO)(EO)(EO); (PO)(EO)(PO); (PO)(PO)(EO) and (PO)(PO)(PO). Of course, the integer three is chosen for example only and the variation may be much larger with a higher integer value for x and include, for example, multiple (EO) units and a much smaller number of (PO) units. Similarly, ethylene, and propylene are chosen for example only and the variation may be much larger with selection of linear or branched butylene, pentylene, hexylene and/or heptylene. Preferably, x is from about 2 to about 20, and each $R^1$ is ethylene or propylene. More preferably, x is from about 4 to about 12, and each $R^1$ is ethylene.

The ether-capped poly(oxyalkylated) alcohols used in the compositions of the present invention can be prepared via a variety of different processes. In one aspect of the present invention, the ether-capped poly(oxyalkylated) alcohol may be prepared by the following steps: (a) providing a vinyl ether of the formula:

wherein $R^2$ is as defined above; (b) providing an alkoxylated alcohol of the formula

wherein R, $R^1$, and x, are as defined above; and (c) reacting the vinyl ether and alkoxylated alcohol in the presence of a catalyst to form the ether-capped poly(oxyalkylated) alcohol.

In one embodiment of this aspect of the present invention the step of reacting of vinyl ether with alkoxylated alcohol is conducted in the presence of a catalyst. Suitable catalysts include Lewis acids; acids and their salts, both organic and inorganic; pyridinium salts; polymers; clays, such as Spanish sepiolite clay, GIRDLER K-10; aluminosilicates or zeolites, such as HZS-360 zeolite, H—Y zeolite; activated carbon, such as sulfonated charcoal; transition metal complexes, such as molybedenyl(VI) acetylacetone; transition metal salts, such as lanthum trichloride, ceric ammonium nitrate; 2,3-dichloro-5,6,dicyano-p-benzoquinone; bis(trimethysilyl)sulfate; and mixtures thereof.

Suitable Lewis acids include, but are not limited to, $TiCl_4$, $Ti(O^iPr)_4$, $ZnCl_2$, $SnCl_2$, $AlCl_3$, platinum dichloride, copper (II) chloride, phosphorous pentachloride, phosphorous trichloride, cobalt(II) chloride, zinc oxide, iron(II) chloride and $BF_3$-$OEt_2$.

Suitable inorganic acids and salts include mineral acids, such as, phosphoric acid, sulfuric acid, hydrochloric acid, phosphorous oxychloride, aluminium phosphate and ammonium chloride. Furthermore, the mineral acids or their salts can optionally be adsorbed onto a substrate, such as silica gel, or alumina. For example sulfuric acid can be adsorbed on silica gel, or alumina impregnated with zinc chloride.

Suitable organic acids include: carboxylic acids, such as acetic acid, oxalic acid, glycolic acid, citric acid, tartaric acid, maleic acid and oxydisuccinic acid; halogenated carboxylic acids, such as trifluoroacetic acid, heptafluorobutyric acid, dichloroacetic acid, and trichloroacetic acid; and sulfonic and sulfinic acids and their salts such as p-toluenesulfonic acid, p-toluenesulfinic acid, methanesulfonic acid, trifluoromethanesulfonic acid, 4-bromobenzenesulfonic acid, naphthalenesulfonic acid, (±)-10-camphorsulfonic acids, xylenesulfonic acid, cumenesulfonic acid, and alkylbenzene sulfonic acid.

Suitable pyridinium salts include, but are not limited to, pyridinium p-toluenesulfonate (PPTS), pyridinium p-toluenesulfinate, pyridinium hydrochloride, pyridinium hydrobromide, pyridinium hydrogen bisulfate, pyridinium hydrogen sulfate and mixtures thereof.

Suitable transition metal complexes include, but are not limited to, molybedenyl(VI) acetylacetone; transition metal salts, such as lanthum trichloride, ceric ammonium nitrate; 2,3-dichloro-5,6,dicyano-p-benzoquinone, mercury(II) acetate, mercury(II) trifluroacetate, copper(II) acetylacetonate and tetracarbonylbis(cyclopentadienyl)diiron.

Suitable polymers include, but are not limited to, polymeric ion exchange resins, or polyvinyl pyridines. Suitable polymeric ion exchange resins include those of the Amberylst series, such as AMBERYLST®15, available from Rohm & Haas, the DOWEX® series, such as DOWEX 50X8-50 avaliable from Dow; REILLEX 424, available from Reilly Industries; the Amberlite series, such as AMBERLITE IRA-400, or AMBERLITE IR-118, available from Rohm & Haas; the ENVIROCAT series, such as ENVIROCAT EPZG, available from Contract Chemicals; and combinations thereof. Suitable polyvinyl pyridines can be unsubstituted or substituted, such as substituted on the vinyl group and/or on the pyridine ring. Examples of suitable polyvinyl pyridines include, but are not limited to, poly(4-vinylpyridine trifluoromethanesulfonate), poly(2-vinylpyridine trifluoromethanesulfonate), poly(4-vinylpyridine p-toluenesulfonate), poly(2-vinylpyridine p-toluenesulfonate), poly(4-vinylpyridine chloride), poly(2-vinylpyridine chloride), poly(4-vinylpyridine bromide), poly(2-vinylpyridine bromide), and mixtures thereof. These polymeric catalysts have the additional advantage of being easy to separate from the surfactant produced.

Other suitable catalysts include bis(trimethysilyl)sulfate, iodotrimethylsilane, allytrimethyl silane, hexamethyldisilane, iodine, bromine, iron(II) sulfate, triphenylphosphine, aluminium sulfate, alkylether sulfuric acids, alkyl sulfuric acids, lithium perchlorate, lithium tetrafluoroborate, acetonyltriphenylphosphonium bromide, zirconium hydroxide, potassium cyanide, and platinum oxide.

Preferred catalysts include the sulfonic acids, Lewis acids, polyvinyl pyridines, methanesulfonic acid, AMBERYLST®15, acidic versions of DOWEX® and pyridinium p-toluenesulfonate (PPTS), with polyvinyl pyridines, pyridinium p-toluenesulfonate (PPTS), p-toluenesulfonic acid, DOWEX®, AMBERYLST®15 and methanesulfonic acid being the most preferred.

Mixtures of catalysts are also within the scope of the present invention. Similarly, the uses of supported, such as in a column for a continuous reaction, and unsupported catalysts are also within the scope of the present invention.

The catalysts are preferably employed at amounts of about 0.005 mol % to about 20.0 mol %, more preferably from about 0.01 mol % to about 10.0 mol %, even more preferably from about 0.01 mol % to about 5.0 mol %, even more preferably still from about 0.01 mol % to about 2.0 mol %, even more preferably still from about 0.01 mol % to about 1.5 mol %, based on the number of moles of alkoxylated alcohol in step (c) of the process. Other suitable catalysts can be found in U.S. Pat. No. 4,272,394, and in PCT publications, WO 94/22800, WO 93/04153, WO96/00253 and WO 98/17379, all of which are incorporated herein by reference.

In one embodiment of this aspect of the present invention the reaction is conducted in the presence of a solvent, or mixtures of solvents. It is preferred that the solvent be a polar aprotic solvent. Suitable solvents include, but are not limited to, hexane, benzene, toluene, xylene, mesitylene, dichloromethane, tetrahydrofuran, dioxane, diethylether, methyl tert-butylether, acetone, acrylonitrile, or the like. Furthermore, the reaction is preferably conducted at temperatures ranging from about −20° C. to about 300° C., more preferably from about −10° C. to about 250° C., and most preferably from about 10° C. to about 60° C. Lastly, the reaction is preferably conducted at pressures ranging from about 0.5 atmospheres to about 100 atmospheres, and more preferably from about 0.8 atmospheres to about 10 atmospheres.

In another embodiment of this aspect of the present invention the step of reacting vinyl ether with alkoxylated alcohol is conducted in the absence of a solvent.

Further disclosure on suitable solvents and catalysts can be found in "Advanced Organic Chemistry", by Jerry March, $4^{th}$ ed., Wiley-Interscience, 1992, "Comprehensive Organic Transformations" by Richard C. Larock, VCH Publishers, 1989, and "Protective Groups in Organic Synthesis" $3^{RD}$ ed. by Theodora W. Greene and Peter G. M. Wuts, Wiley-Interscience, 1999 the relevant portions of which are incorporated herein by reference.

In one embodiment of the present invention, the process is performed as a batch process. That is, the reaction is let to proceed to completion, or near completion, and then final product is removed. In another embodiment of the present invention, the process is performed as a continuous process. That is, the product of the process is continuously removed from the reaction vessel while starting material is added at a comparable rate.

In one embodiment of the present invention the vinyl ether is reacted with the alkoxylated alcohol at a mole ratio of from about 5:1 to about 0.5: 1, more preferably from about 3:1 to about 0.75:1, more preferably still from about 1.5:1 to about 0.9:1.

In one embodiment of the process of the present invention the process may be conducted in an inert gas. This may be done by sparging with any suitable inert gas, such as nitrogen, helium, neon, argon or the like.

In one embodiment of the present invention reaction step (c) above may be followed by optional step (d). Step (d) is a step in which the reaction step (c) is quenched, preferably by the addition of base. The amount of the ether capped poly(oxyalkylated) alcohol present in the reaction mixture will depend upon many factors, including but not limited to, starting materials, temperature, catalyst selection and the like. Quenching stops the reaction of the starting materials, and ensures that any ether capped poly(oxyalkylated) alcohol produced does not undergo further reaction or revert back to the starting materials. The quenching of step (c) produces a mixture which contains ether capped poly (oxyalkylated) alcohol, as well as unreacted starting materials, catalyst and the products of any side reactions. In one embodiment of this present invention, the quenching of the reaction of step (c) is done when the reaction mixture preferably contains at least 90%, more preferably at least 95% by weight of ether capped poly(oxyalkylated) alcohol. The remaining portion of the mixture, up to 10%, more preferably up to 5% by weight, comprises unreacted starting material as well as products of side reactions, such as byproduct acetals. In one aspect of this embodiment of the present invention the base may be optionally selected from the group consisting of alkali metal carbonates, alkali metal bicarbonates, alkali metal hydroxides, alkali metal alcoholates, alkanolamines, alkylamines, aromatic amines and mixtures thereof. In a further aspect of the present invention the base may be optionally selected from the group consisting of potassium carbonate, sodium carbonate, sodium bicarbonate, sodium methoxylate, sodium ethoxylate, potassium tert-butyloxylate, triethylamine, triethanolamine and mixtures thereof. In another aspect of this embodiment of the present invention, the base may be in the form of an aqueous solution. In a further aspect of this embodiment of the present invention, the aqueous solution may be at a temperature of from about 20° C. to about 60° C.

The expression "product of step (c)" is meant to include not only the ether-capped poly(oxyalkylated) alcohol but also any unreacted starting materials or any materials produced from side reactions, such as dimers, which would be present at the conclusion of step (c).

In one embodiment of the present invention the process of the present invention may optionally further comprise a step (e). Step (e) is removal of color bodies and/or odors from the product of steps (c) or (d). In one aspect of this embodiment of the present invention removal of the color bodies and/or odors is obtained by contacting the product of steps (c) or (d) with a reagent. The reagent can either be an oxidant, or a reductant. Suitable oxidants include hydrogen peroxide. Suitable reductants include sodium borohydride, and hydrogen over a palladium/carbon catalyst. In a further aspect of this embodiment of the present invention the color bodies and/or odors are removed by contacting the product of step (c) first with an oxidant and then a reductant, or first with a reductant and then an oxidant. The color bodies may also be removed by treating the product mixture with a activated charcoal (carbon).

In one embodiment of the present invention the ether-capped poly(oxyalkylated) alcohol produced in steps (c) or (d) may optionally be removed from the product of steps (c) or (d) by centrifuging.

Some representative examples of this possible synthetic route of this aspect of the invention are demonstrated via the following diagrams.

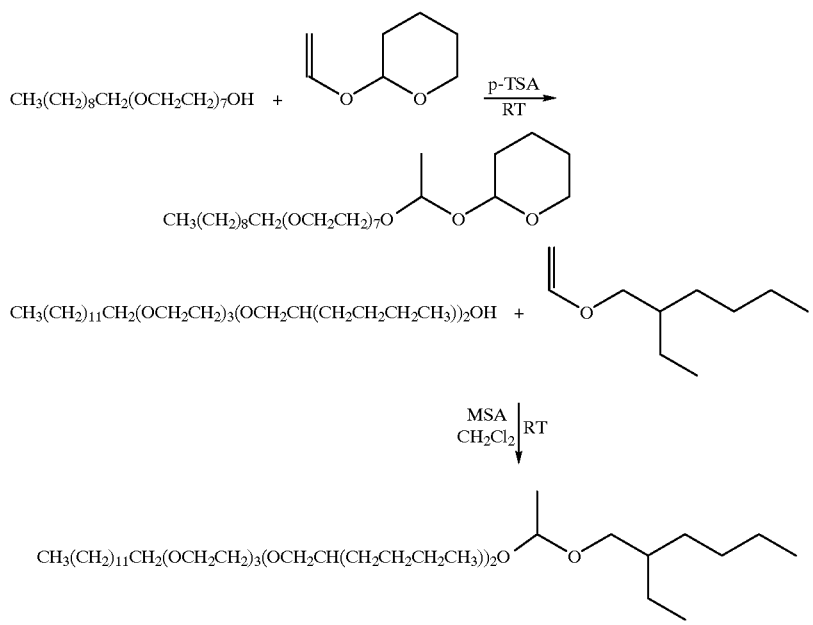

The ether-capped poly(oxyalkylated) alcohol product is then collected by means common in the art such as extraction. If so desired, stripping, distillation or various other means may be used to treat the ether-capped poly (oxyalkylated) alcohol product before use. The ether-capped poly(oxyalkylated) alcohols made by the process disclosed herein may contain related impurities, which will not adversely affect performance.

Compositions and Methods

The ether-capped poly(oxyalkylated) alcohol wetting agents of the present invention may be used in a variety of applications, such as antifoaming agents, in drilling muds, etc., in a wide range of fields, such as in biocides, meat cleaning, foods, pharmaceuticals, polymer latexes, etc. The ether-capped poly(oxyalkylated) alcohol wetting agents have the properties of good biodegradability, low-sudsing as well as cleaning which allows them to be used in a wide range of diverse and radically different applications. For any particular application which desires a specific physical property, such as HLB or cloud point, an ether-capped poly(oxyalkylated) alcohol surfactant, or mixtures of ether-capped poly(oxyalkylated) alcohol surfactant, may be used. The desired propertied are obtained varying the selection of R, $R^1$, x and $R^2$ for any ether-capped poly(oxyalkylated) alcohol surfactant or mixtures of these surfactants. Further examples of possible application for these surfactants can be found in "Nonionic Surfactants" edited by Martin J. Schinck, Surfactant Science Series, Marcel Dekker, NY, Volume 1; "Nonionic Surfactants: Physical Chemistry" edited by Martin J. Schinck, Surfactant Science Series, Marcel Dekker, NY, Volume 23; "Nonionic Surfactants: Polyoxyalkylene Block Copolymers" edited by Vaughn M. Nace, Surfactant Science Series, Marcel Dekker, NY, Volume 60; and L. G. Lundsted and I. R. Schmolka, in "Block and Graft Copolymerization", Vol. 2 (R. J. Ceresa, ed.), John Wiley & Sons, Ltd., London, 1976, pp. 113–272, incorporated herein by reference.

The compositions of the present invention contain an adjunct ingredient. In general, an adjunct is any material required to transform a composition containing only the minimum essential ingredients into a composition useful for the desired end use, such as a fungicidal compound for a fungicide, a dentifrice for a toothpaste, sand for cement, etc. In preferred embodiments, adjuncts are easily recognizable to those of skill in the art as being absolutely characteristic of products, especially of products intended for direct use by a consumer in a domestic environment.

The precise nature of these additional components, and levels of incorporation thereof, will depend on the physical form of the composition and the nature of the operation for which the composition is to be used. The selection of the adjunct will depend upon the type and use of the composition. Non-limiting illustrative examples of compositions including the wetting agents of the present invention as well as suitable adjunct(s) for the illustrative compositions are described hereinafter.

Similarly, the wetting agents of the present invention may also be used in a variety of different methods, with or without any adjunct ingredients. For example, a method of treating waste water from a paper pulp plant involves the addition of one or more of the novel wetting agents of the present invention to improve the treatment of the waste water.

Use levels of the overall compositions can vary widely depending on the intended application, ranging for example from a few ppm in solution to use of the neat composition. Typically, levels of adjuncts are from about 0.00001% to about 99.9%, by weight of the compositions.

Some illustrative compositions of the present invention include:

1. Polymers

The compositions of the present invention may be polymer compositions. That is they may be, for example, polymeric latexes, containing the wetting agent of the present invention as well as monomer and other adjuncts conventionally present. The wetting agents may be present during polymerization to improve the process. For example, a wetting agent could be present in a solution or suspension of monomer to improve the distribution of the monomer in solution and hence increase the rate of polymerization. Alternatively, the wetting aid could be present to affect in some manner the physical properties of the polymer or the polymer composition. The wetting agent may also be used to allow for even distribution, polymerization and/or drying on a surface to which a polymeric dispersion is applied. For example the wetting agents of the present invention could be used to aid in the dispersal of polymeric carpet backing, see WO 99/52968 filed Apr. 14, 1998, or to emulsify polymeric compositions which are applied to fabrics, see U.S. Pat. No. 4,088,592. Another example is that the wetting agent of the present invention may be used in the production of, and present in polymeric films and laminates, especially films for stretch wrapping. See U.S. Pat. No. 4,066,811, Naito et al, granted Jan. 3, 1978. See also Daeumer et al., issued Sep. 20, 1994.

In such polymeric compositions common adjutants include, but are not limited to, monomers, fillers, solvent, flame retardant, cross-linking agents, preservatives, pigments, catalysts, co-catalysts, anti-foaming agents, resins, viscosity control agents, wetting agents other than those of the present invention, polymers, initiators, chain transfer agents, anti-oxidants, UV absorbers and mixtures thereof.

2. Anti-Foaming/Suds Suppressors

The wetting agents of the present invention may be used as partial or total replacements for convention anti-foaming compositions. At present most, if not all, commercial anti-foaming compositions are based around one or more silicon containing compounds. While these provide adequate anti-foaming, they are expensive and typically a complex mixture of silicon containing compounds as well as other ingredients. The wetting agents of the present invention have none of these disadvantages associated with conventional anti-foams. Furthermore, the wetting agents of the present invention have the added advantage of being readily biodegradable.

The wetting agents of the present invention may be used as foam control additives in a variety of applications, such as food, agriculture, and paper. They also carry the added advantage of being able to control foaming while also acting as a wetting agent. This dual advantage of these wetting agents allows for them to replace two components in a composition with a single one that provide both the properties desired. Similarly, the wetting agents of the present invention may be used in a method for reducing or controlling the foaming of a composition by adding a foam reducing/controlling amount of a wetting agent of the present invention. Further information on foam control compositions and their applications can be found in U.S. Pat. No. 5,990,181 to Spyropoulos et. al., issued Nov. 23, 1999 and U.S. Pat. No. 5,843,734 to Shonaka et. al., issued Dec. 1, 1998; and WO 98/00216 to Rhone-Poulenc, published Jan. 8, 1998, and WO 98/30305 to Henkel Corporation, published Jul. 16, 1998.

3. Biocidal Compositions

The wetting agents of the present invention may also be used in biocidal compositions. Biocidal compositions are compositions that have some desired effect on a biological system or organism, such as killing the organism, preventing its reproduction etc. They can be targeted at one specific organism, such as termites, or be designed to act on a wide range of organisms, such as an insecticide. Typically the biocidal compositions contain a biocide or biocides that provide the desired effect on the biological system or organism. Some illustrative example of some biocidal compositions include, but are not limited to, insecticides, miticides, aphicides, fungicides, bacteriocides, molluscicides, acaricides, nematicides, fugicides, plant growth regulators, defoliants, gametocides, herbicides, algicides, viricides, dessicants, insect repellents and the like.

The wetting agents of the present invention may be used in the biocidal composition in many ways. They may, for example, be used to improve delivery of the biocide onto the target organism, improve the dispersion in the composition of the biocide before delivery, and/or improve the suspension of the biocide in a concentrate formula, which is diluted when used.

The wetting agents of the present invention can be used in biocidal compositions of any form, that is, powder, dusts, granules, liquids, emulsions, suspensions, etc.

In such compositions adjutants include, but are not limited to, fillers, solvent, preservatives, pigments, anti-foaming agents, resins, viscosity control agents, wetting agents other than those of the present invention, polymers, diluents, anti-oxidants, UV absorbers, buffering agents, sticking agents, carriers, biocides, and mixtures thereof.

Suitable biocides include, but are no limited to, insecticides, such as organophosphorus compounds disclosed in U.S. Pat. No. 3,244,586, O,O-diethyl O-(3,5,6-trichloropyridine-2-yl) phosphorothioate, also known as chlorpyrifos, see WO 99/33340 published Jul. 8, 1999 and WO 99/29171 published Jun. 17, 1999; miticides; aphicides; fungicides, such as zinc ethylenebis(dithiocarbamate), nickel dimethyldithiocarbamate, and methyl-1 (butylcarbamoyl)-2-benzimidazolecarbamate, see WO 99/29171 published Jun. 17, 1999; molluscicides; bacteriocides; acaricides, nematicides; plant growth regulators, such as N-methoxycarbonyl-N'-4-methgylphenylcarbamoylethylisourea, sodium napthaleneacetate, triazine herbacieds, such as 2-methylthio-4,6-bisethylamino-1,3,5,-triazine, diphenylether herbicides such as 2,4-dichlorophenyl-4'-nitrophenylether, urea herbicides, carbamate herbicides, thiolcarbamate herbicides, pryrdinium herbicides, analine herbicides, pyrazole herbicides and the like, see WO 99/29171 published Jun. 17, 1999; defoliants, such as agent orange; gametocides; herbicides, such as acetochlor, alachlor, metolachlor, aminotriazole, asulam, bentazon, bialaphos, paraquat, bromacil, clethodium, sethoxydim, dicamba, diflufenican, pendimethalin, acifluorfen, fosamine, flupoxam, bromoxynil, imazaquin, norflurazon, 2,4-D, 2,4, 5-T, diclofop, fluometuron, chlorimuron, triallate, atrazine, salts of N-phosphonomethylglycine (these are also know as the glyphosates, such as in the herbicidal compositions ROUNDUP® and ACCORD® both available from Monsanto, and TOUCHDOWN® available from Zeneca), and monoisopropylamine salts of N-phosphonomethylglycine. Other suitable herbicides may be found in U.S. Pat. No. 6,093,680, Gillespie et al., issued Jul. 25, 2000, and U.S. Pat. No. 4,933,002, Petroff et al., issued Jun. 12, 1990 and in WO 99/33340 published Jul. 8, 1999; algicides; viricides; insect repellents, such as 2-ethyl-1,3-hexanediol, N-octyl bicycloheptene dicarboxamide, N,N-diethyl-M-toluamide, 2,3,4,5-bis(2-butylene) tetrahydro-2furaldehyde; Di-n-propyl isocinchomeronate, 2-hydroxyethyl-n-octyl sulfide, see WO 99/33340 published Jul. 8, 1999; and mixtures thereof.

The amount of biocide present as well as other ingredients will depend upon not only the target biological system or organism, but also on the location of the organism as well as the means for delivery of the biocidal composition.

Additional information on biocides, biocidal compositions as well as their formulation and delivery can be found in U.S. Pat. No. 4,565,162 Itho et al, issued Apr. 7, 1987; U.S. Pat. No. 4,933,002 Petroff et al., issued Jun. 12, 1990; U.S. Pat. No. 5,332,714 Albrecht et al., issued Jul. 26, 1994; U.S. Pat. No. 5,389,300 Schmitt et al., issued Feb. 14, 1995; U.S. Pat. No. 5,580,840 Harms et al., issued Dec. 3, 1996; U.S. Pat. No. 5,874,096 Hazen issued Feb. 23, 1999; U.S. Pat. No. 5,968,872 Policello et al., issued Oct. 19, 1999; U.S. Pat. No. 6,051,730 Pallas et al issued Apr. 18, 2000; and U.S. Pat. No. 6,093,680 Gillespie et al., issued Jul. 25, 2000; and WO applications 98/17108 published Apr. 30, 1998; 99/29171 published Jun. 17, 1999; 99/33340 published Jul. 8, 1999; and 99/40784 published Aug. 19, 1999.

4. Cements

The wetting agents of the present invention may be used in cement admixtures. The wetting agents may be, for example, present to suspend or disperse ingredients present in the composition, or they may be present to affect the drying rate of the cement or affect the physical properties of the final cement product in some fashion, such as inhibiting shrinkage on drying, or affecting the distribution, size and shape of air entrapped in concrete or mortar. The term cements is intended to cover all similar materials, whether predominately organic or inorganic, such as concrete, mortars, hydraulic cements, and the like. The wetting agents of the present invention are suitable for use in both inorganic cements, such as Portland cement, and in predominately organic cements, such as the styrene/butadiene latex of U.S. Pat. No. 5,300,542 Gopalkrishan issued Apr. 5, 1994.

Typical adjunct ingredients found in cement include, but are not limited to, aggregate, sand, water, shrinkage inhibitors, hardening accelerants, fluid loss control agents, retardants, light weight additives, heavy weight additives, binders, defoamers, solvent, wetting agents other than the wetting agents of the present invention, dyes, pigments, fillers, fluidizing agents, corrosion inhibitors, air entraining agents, polymers, and mixtures thereof. See U.S. Pat. No. 5,779,788 Berke et al., issued Jul. 14, 1998, U.S. Pat. No. 5,085,708 Myoria et al., issued Feb. 4, 1992, U.S. Pat. No. 5,207,831 Cowan issued May 4, 1993, U.S. Pat. No. 5,348, 993 Daeumer et al., issued Sep. 20, 1994, and U.S. Pat. No. 5,300,542 Gopalkrishan issued Apr, 5, 1994, U.S. Pat. No. 5,922,796 Colombet et al, issued Jul. 3, 1999 and WO99/65841 W. R. Grace & Co., published Dec. 23, 1999.

5. Coating Compositions

The wetting agents of the present invention can be used in coating compositions such as paints, rust treatments/inhibitors, undercoats, lacquers, varnishes and the like. The wetting agents may, for example, be used to suspend or aid in suspension of some or all of the components of the compositions, aid in even application or distribution of the components on a surface, increase the speed of drying or make drying uniform or more even. The composition may be water or oil based and they may be applied to a surface via brush, roller, aerosol, spray booth, or similar electrostatic spray means.

By coating compositions it is meant a variety of composition for application to a surface to coat the surface, such as paints, inks, primers, sealants, adhesives and the like. The coating composition may be applied to a variety of surfaces. For example, suitable surfaces include wood, metal, glass, plastic, laminates, cement and the like.

Typical adjunct ingredients found in coating compositions include, but are not limited to, monomers, fillers, pigments, solvents, dyes, flame retardants, cross-linking agents, preservatives, pigments, catalysts, co-catalysts, anti-foaming agents, resins, viscosity control agents, wetting agents other than those of the present invention, polymers, anti-oxidants, UV absorbers, conditioning agents, biocides, fungicides, light stabilizers, anti-oxidants, reducing agents, corrosion inhibitors, carriers, rheology modifiers, propellants, plasticizers, buffers, initiators, chain transfer agents, wood preservatives, and mixtures thereof. See U.S. Pat. No. 5,389,300 Schmitt et al., issued Feb. 14, 1995; U.S. Pat. No. 5,348,993 Daeumer et al., issued Sep. 20, 1994; U.S. Pat. No. 5,922,796 Colombet et al, issued Jul. 13, 1999; U.S. Pat. No. 5,157,069 Campbell issued Oct. 20, 1992; U.S. Pat. No. 4,265,797 Suk issued May 5, 1981, U.S. Pat. No. 6,060,556 Collins et al., issued May 9, 2000; U.S. Pat. No. 5,601,879 Anchor et al., issued Feb. 11, 1997; U.S. Pat. No. 5,681,880 Desor et al., issued Oct. 28, 1997; U.S. Pat. No. 5,880,190 Laura issued Mar. 9, 1999; U.S. Pat. No. 4,639,475 Dierichs et al., issued Jan. 27, 1987; U.S. Pat. No. 4,765,243 Schiefer et al., issued Aug. 23, 1988; WO 99/10464 Amway, published Mar. 4, 1999; WO 99/09104 Eastman Chemical Company, published February 1999; and WO 00/18484 Ashland Inc., published Apr. 6, 2000, 6. Fertilizers The wetting agents of the present invention may be used in fertilizer compositions. By fertilizer compositions it is meant compositions that provide nutrients, food or the like to plants or that are designed to increase resistance to some pest or disease. They may be in the form of tablets, granules, powders, liquids, pastes, emulsions, suspensions, concentrates and the like.

Typical adjunct ingredients found in fertilizer compositions include, but are not limited to, trace elements, binders, wetting agents other than the wetting agents of the present invention, filler, thickener, preservative, blood and bone products, ammonium nitrates, lime, sand, sources of nitrogen, buffers, nitrification inhibitors, growth hormones, antibiotics, soil-improving components, humus, peat, potassium, phosphorous, solvent, carrier, defoaming agents, micronutrients, and mixtures thereof. See U.S. Pat. No. 5,482,529 Ahlnas et al., issued Jan. 9, 1996; U.S. Pat. No. 4,345,931 Meyer issued Aug. 24, 1982; U.S. Pat. No. 4,055,974 Jackson issued Nov. 1, 1997; and WO 98/39237 published Sep. 11, 1998.

7. Pharmaceuticals

The wetting agents of the present invention may be used in pharmaceutical compositions. They may be used to improve the dissolution of a medicament, such as in an oral suspension, enema or suppository, or may be used in the preparation of the pharmaceutical composition. The pharmaceutical compositions may be in any conventional form, such as suspension, powder, granule, tablet, capsule, caplet, suppository, lotion, cream, aerosols, emulsions, microemulsions, vapor, inhalant, liquid (such as those taken orally, nasally or through any other mucus membrane, subcutaneously or intramuscularly), adhesive patch and the like.

Typical adjunct ingredients found in pharmaceutical compositions include, but are not limited to, medicaments, fillers, lubricants, coating agents, buffers, adhesives, gelling agents, mould release agents, flavorings, sweeteners, carriers, stabilizers, humectants, coloring agents, extenders, preservatives, wetting agents other that the wetting agents of the present invention, solvent, electrolytes, and mixtures thereof. See U.S. Pat. No. 5,646,109 Owen et al., issued Jul. 8, 1997, U.S. Pat. No. 5,626,879 Anaebonam et al, issued May 6, 1997, and U.S. Pat. No. 5,897,548 Sacco et al, issued Apr. 27, 1999 and WO 94/07472 Pfizer, published Apr. 14, 1994.

8. Toothpastes

The wetting agents of the present invention may also be used in toothpastes, and/or associated oral hygiene products, such as dental rinses, moth washes, or in any other composition/product/process associated with dental hygiene that would be used at home or by a dental surgeon/technician, such as a fluoride gel. The wetting agents may be used, for example, in the processing/preparation of toothpaste, or to aid in suspension of one or more of the components of the tooth paste and/or improve mouth feel and foam quality during use.

Typical adjunct ingredients found in toothpastes include, but are not limited to, medicaments, dentifrices, abrasives, sources of fluorine, fillers, lubricants, coating agents, buffers, adhesives, gelling agents, polishing agents, antibacterial agents, flavorings, sweeteners, carriers, solvents, stabilizers, opacifying agents, coloring agents, extenders, preservatives, polymers, anti-calculus agents, dyes, iridescent particles, essential oil, wetting agents other that the wetting agents of the present invention, defoamers, solvent, humectants, electrolytes, binders, thickeners, rheology modifiers, and mixtures thereof. See U.S. Pat. No. 5,723,105 Viscio et al., issued Mar. 3, 1998, and WO 98/55084, Block Drug Company, published Dec. 10, 1998.

9. Metal Cleaners

The wetting agents of the present invention may also be used in metal cleaning compositions. The term "metal cleaning" compositions is meant to include not only compositions which are used for degreasing metal surfaces, but also to include compositions which are used in cleaning electronic/electric components, such as those compositions used in clean rooms, metal cutting fluids, and the like. The compositions may be of any conventional form, such as liquid, emulsion, microemulsion, azeotrope, azeotrope like, and the like.

Typical adjunct ingredients found in metal cleaning compositions include, but are not limited to, abrasives, coating agents, buffers, gelling agents, polishing agents, carriers, solvents, stabilizers, coloring agents, polymers, wetting agents other that the wetting agents of the present invention, defoamers, electrolytes, thickeners, rheology modifiers, and mixtures thereof. See U.S. Pat. No. 4,091,826 Bahrke issued May 30, 1978; U.S. Pat. No. 4,778,532 McConnell et al., issued Oct. 18, 1998; U.S. Pat. No. 5,503,681 Inada et al., issued Apr. 2, 1996; U.S. Pat. No. 5,628,833 McCormack et al. issued May 13, 1997; and EP Patent Application No. 971000 to Tokyo Electron Limited, published Jan. 12, 2000.

10. Paper Processing

The wetting agent of the present invention may also be used in both the processes for preparing paper as well as treatment of waste material produced during these processes. The wetting agents of the present invention may be used during the preparation of paper, for example, to increase the tactile softness of the paper, or to improve the wetting and or dispersion of the components as needed. Additionally, the wetting agents of the present invention may be used to control the foam generation in any liquids used in the paper making process, especially foaming any waste liquids, such as black liquor. See WO 97/35067 Betzdearbom Inc, published Sep. 25, 1997.

The present invention also provides for a method of adding a wetting agent according to the present invention to a liquid or composition associated with a papermaking process to reduce, control or eliminate any foam produced by the liquid or composition. See WO 97/35067 Betzdearbom Inc, published Sep. 25, 1997, WO 94/05856 published Mar. 17, 1994 and U.S. Pat. No. 5,660,684 Li et al., issued Aug. 26, 1997.

11. Drilling Fluids

The wetting agents of the present invention may also be used in drilling fluids, or so-called drilling muds. A drilling fluid may be circulated down through the drill pipe, out the drill bit and back up to the surface through the annulus between the drill pipe and the borehole wall. The drilling fluid has a number of purposes, including cooling and lubricating the bit, carrying the cuttings from the hole to the surface and exerting hydrostatic pressure against the borehole wall to prevent the flow of fluids from the surrounding formation into the borehole.

A drilling fluid with relatively high viscosity at high shear rates can place undesirable mechanical constraints on the drilling equipment and may even damage the reservoir. Higher viscosity fluids also exert higher pressures outward on the borehole, which may cause mechanical damage to the formation and reduce the ability of the well to produce oil and/or gas. Higher viscosity fluids may also fracture the formation, requiring a drilling shutdown in order to seal any fractures. Damage to a reservoir is particularly harmful if it occurs while drilling through the "payzone", or the zone believed to hold recoverable oil or gas. In order to avoid such damage, a different fluid, known as a "drill-in" fluid, is pumped through the drill pipe while drilling in the pay zone.

Another type of fluid used in oil and gas wells is a "completion fluid". A completion fluid is pumped down a well after drilling operations are completed during the "completion phase". Drilling mud is typically removed from the well using "completion fluid". Then, the equipment required to produce fluids, oil or gas, to the surface is installed in the well.

The wetting agents of the present invention are suitable for use in all types of drilling fluids, such as drilling muds, "drill-in" fluids and "completion" fluids.

Typical adjunct ingredients found in drilling fluids include, but are not limited to, defoamers, solvent, wetting agents other than the wetting agents of the present invention, corrosion inhibitors, polymers, brine, viscosity agents, rehology agents, water soluble polymers, drilled solids, clay, weighting materials, gelling agents, fluid loss additives, and mixtures thereof. See U.S. Pat. No. 5,300,542 Gopalkrishan issued Apr. 5, 1994, WO 98/42795 published Oct. 1, 1998 and 00/26321 published May 11, 2000.

12. Miscellaneous

The wetting agents of the present invention may also be used in a variety of compositions or applications. Examples of these include, but are not limited to:

Lens Cleaners

The wetting agents may be used in composition and/or methods for cleaning lenses, such as spectacles, contact lenses (including hard lenses, rigid gas permeable and soft type lenses) and the like. Adjuncts that may be used in these compositions include, but are not limited to, solvents, buffer, abrasives, enzymes, enzyme inhibitors, anti-bacterial agents, germicides, preservatives, humectants, wetting agents other than the wetting agent of the present invention, tonicity agents, viscosity builders, and mixtures thereof. See WO 99/43363 Bausch & Lomb Inc, published Sep. 2, 1999.

Furthermore, these wetting agents of the present invention may also be used in the compositions and/or processes for the manufacture or polishing of lenses. See U.S. Pat. No. 4,546,123 Schafer et al., issued Oct. 8, 1985.

Other Applications

The wetting agent of the present invention may be used in leather care compositions, see U.S. Pat. No. 4,554,083 Soldanski et al., issued Nov. 19, 1985; compositions for the suppression of dust or in ore flotation, see U.S. Pat. No. 5,412,007 Hendrix et al., issued May 2, 1995 and U.S. Pat. No. 4,746,543 Zikan et al., issued May 24, 1988; compositions for printers and photocopies, such as ink jet compositions, see U.S. Pat. No. 4,680,332 Hair et al., issued Jul. 14, 1987; in foods, see U.S. Pat. No. 4,752,485 Sharma et al., issued Jun. 21, 1998; in explosives, especially in oil-in-water emulsion explosives, see U.S. Pat. No. 4,784,706 McKenzie issued Nov. 15, 1988; in photography, especially in photographic emulsions, see U.S. Pat. No. 5,215,873 Kiesslich et al., issued Jun. 1, 1993; emulsification of silicones, see U.S. Pat. No. 5,338,352 Breneman et al., issued Aug. 16, 1994; in dyes or dying compositions/solutions, see U.S. Pat. No. 5,360,457 Ruggiero et al, issued Nov. 1, 1994; in catalysts, and in their manufacture and preparation, see U.S. Pat. No. 5,958,819 Johnson et al., issued Sep. 28, 1999; in ice melting and defogging compositions, see U.S. Pat. No. 6,039,890 Ossian et al., issued Mar. 21, 2000; and in the preparation and manufacture of diaphragms for electrolytic cells, see U.S. Pat. No. 6,059,944 Dubois et al., issued May 9, 2000.

It is to be understood that the above illustrative compositions, methods and processes are to be in no way construed as limiting of the scope of the present invention. They are merely illustrative of some and not all of the possible uses the wetting agents of the present invention.

All documents cited are in relevant part, incorporated herein by reference.

The following examples are illustrative of the present invention, but are not meant to limit or otherwise define its scope. All parts, percentages and ratios used herein are expressed as percent by weight unless otherwise specified.

EXAMPLES

Example 1

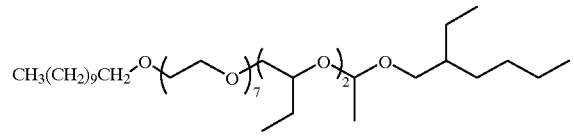

Preparation of $C_{11}H_{23}O(C_2H_4O)_7 (C_4H_8O)_2$2-ethylhexyl Acetal

Neodol 1-7 (20.00 g, 41.6 mmol) is placed into a 500 ml three-necked round-bottomed flask, fitted with a heating mantle, magnetic stirrer, internal thermometer and argon inlet and dried under vacuum at 75° C. After releasing the vacuum with argon, sodium metal (0.05 g, 2.1 mmol) is added and the mixture stirred for 1 hour at 120° C. After increasing the reaction temperature to 140° C., 1,2-epoxybutane (6.00 g, 83.2 mmol) is added dropwise over 30 minutes. After the addition is complete the mixture is stirred for an additional 1 hour at 140° C. The solution is cooled to 90° C. and neutralized with concentrated HCl. After removing water and the last traces of 1,2-epoxybutane under vacuum and cooling to ambient, methylene chloride (200 ml) and 2-ethylhexyl vinyl ether (19.49 g, 124.7 mmol) are added. The mixture is cooled to 0° C. and pyridinium p-toluenesulfonate (0.42 g, 1.7 mmol) is added. The mixture is first stirred 4 hours at 0° C. and then 18 hours at ambient. After diluting with diethyl ether (200 ml), the mixture is washed twice with saturated sodium bicarbonate and the organic layer dried with sodium sulfate/potassium carbonate. The product was concentrated by rotary evaporation and dried under vacuum in the presence of potassium carbonate to yield a yellow liquid.

Example 2

Examples 2(a) to (j) are illustrative of some of the possible catalysts, work up options and relative amounts the starting materials which can be used in the present invention.

Example 2(a)

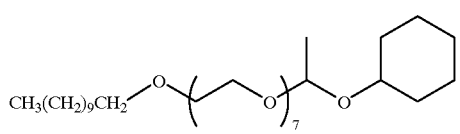

Preparation of $C_{11}H_{23}O(C_2H_4O)_7$-cyclohexyl Acetal
Neodol 1-7 (50.00 g, 104.0 mmol) is placed into a 1000 ml three-necked round-bottomed flask, fitted with a heating mantle, magnetic stirrer, internal thermometer and argon inlet and dried under vacuum at 75° C. After cooling to ambient and releasing the vacuum with argon, methylene chloride (500 ml) and cyclohexyl vinyl ether (39.36 g, 311.9 mmol) are added. The mixture is cooled to 0° C. and pyridinium p-toluenesulfonate (1.04 g, 4.2 mmol) is introduced into the flask. The mixture is first stirred 4 hours at 0° C. and then 18 hours at ambient. The product mixture is then washed twice with saturated sodium bicarbonate and the organic layer dried with magnesium sulfate, concentrated by rotary evaporation and further stripped under vacuum at 60° C. (0.1 mmHg) to yield a liquid.

Example 2(b)

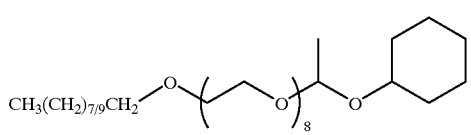

Preparation of $C_{9/11}H_{19/23}O(C_2H_4O)_8$-cyclohexyl Acetal
Neodol 91-8 (20.00 g, 39.1 mmol) and poly(4-vinylpyridinium p-toluenesulfonate) (0.43 g) are introduced into a 250 ml three-necked round-bottomed flask, fitted with a heating mantle, magnetic stirrer, internal thermometer and argon inlet and dried under vacuum at 75° C. After cooling to ambient and releasing the vacuum with argon, cyclohexyl vinyl ether (4.94 g, 39.1 mmol) is added. The mixture is heated to 70–95° C. overnight. The product mixture is filtered to yield a liquid.

Example 2(c)

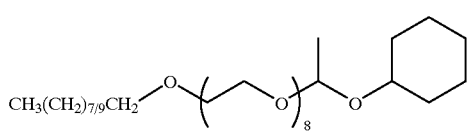

Preparation of $C_{9/11}H_{19/23}O(C_2H_4O)_8$-cyclohexyl Acetal
Neodol 91-8 (20.00 g, 39.1 mmol) and poly(4-vinylpyridinium p-toluenesulfonate) (0.43 g) are introduced into a 250 ml three-necked round-bottomed flask, fitted with a heating mantle, magnetic stirrer, internal thermometer and argon inlet and dried under vacuum at 75° C. After cooling to ambient and releasing the vacuum with argon, cyclohexyl vinyl ether (4.94 g, 39.1 mmol) is added. The mixture is heated to 70–95° C. overnight. The product mixture is separated from the catalyst by centrifugation to yield a liquid.

Example 2(d)

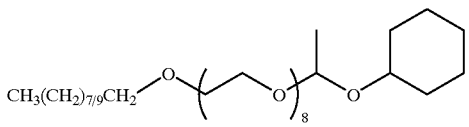

Preparation of $C_{9/11}H_{19/23}O(C_2H_4O)_8$-cyclohexyl Acetal
Neodol 91-8 (20.00 g, 39.1 mmol) and poly(4-vinylpyridinium p-toluenesulfonate) (0.43 g) are introduced into a 250 ml three-necked round-bottomed flask, fitted with a heating mantle, magnetic stirrer, internal thermometer and argon inlet and dried under vacuum at 75° C. After cooling to ambient and releasing the vacuum with argon, cyclohexyl vinyl ether (4.94 g, 39.1 mmol) is added. The mixture is heated to 70–95° C. overnight. The product mixture is washed with 20% potassium carbonate solution, dried and filtered to yield a liquid.

Example 2(e)

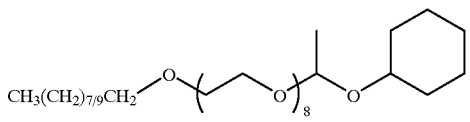

Preparation of $C_{9/11}H_{19/23}O(C_2H_4O)_8$-cyclohexyl Acetal
Neodol 91-8 (20.00 g, 39.1 mmol) is placed into a 250 ml three-necked round-bottomed flask, fitted with a heating mantle, magnetic stirrer, internal thermometer and argon inlet and dried under vacuum at 75° C. After cooling to ambient and releasing the vacuum with argon, methylene chloride (100 ml) and cyclohexyl vinyl ether (5.43 g, 43.01 mmol) are added. The mixture is cooled to 0° C. and pyridinium p-toluenesulfonate (0.43 g, 1.6 mmol) is introduced into the flask. The mixture is first stirred 4 hours at 0° C. and then 18 hours at ambient. The product mixture is then washed twice with saturated sodium bicarbonate and the organic layer dried over sodium carbonate, concentrated by rotary evaporation and further stripped under vacuum at 60° C. (0.1 mmHg) in the presence of potassium carbonate to yield a liquid.

Example 2(f)

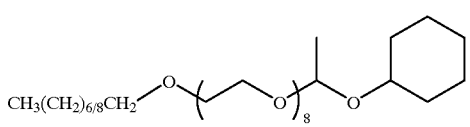

Preparation of $C_{8/10}H_{17/21}O(C_2H_4O)_8$-cyclohexyl Acetal
Alcohol ethoxylate $C_{8/10}H_{17/21}EO_8$ (20.00 g, 40.2 mmol) and poly(4-vinylpyridinium chloride) (2.0 g) are introduced into a 250 ml three-necked round-bottomed flask, fitted with a heating mantle, magnetic stirrer, internal thermometer and argon inlet and dried under vacuum at 75° C. After cooling to ambient and releasing the vacuum with argon, cyclohexyl vinyl ether (5.07 g, 40.2 mmol) is added. The mixture is heated to 70–95° C. overnight. The product mixture is filtered to yield a liquid.

Example 2(g)

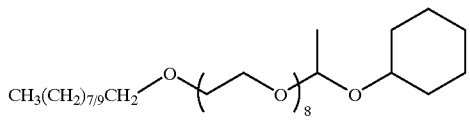

Preparation of $C_{9/11}H_{19/23}O(C_2H_4O)_8$-cyclohexyl Acetal

Neodol 91-8 (20.00 g, 39.1 mmol) and poly(4-vinylpyridinium p-toluenesulfonate) (7.82 g) are introduced into a 250 ml three-necked round-bottomed flask, fitted with a heating mantle, magnetic stirrer, internal thermometer and argon inlet and dried under vacuum at 75° C. After cooling to ambient and releasing the vacuum with argon, acetone (150 mL) and cyclohexyl vinyl ether (4.94 g, 39.1 mmol) are added. The mixture is stirred for three days, filtered and concentrated by rotary evaporation to yield a liquid.

Example 2(h)

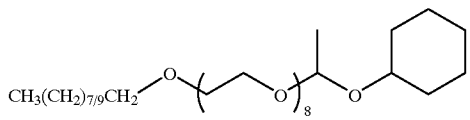

Preparation of $C_{9/11}H_{19/23}O(C_2H_4O)_8$-cyclohexyl Acetal

Neodol 91-8 (20.00 g, 39.1 mmol) is placed into a 250 ml three-necked round-bottomed flask, fitted with a heating mantle, magnetic stirrer, internal thermometer and argon inlet and dried under vacuum at 75° C. After cooling to ambient and releasing the vacuum with argon, methylene chloride (100 ml) and cyclohexyl vinyl ether (4.84 g, 38.4 mmol) are added. The mixture is cooled to 0° C. and pyridinium p-toluenesulfonate (0.39 g, 1.5 mmol) is introduced into the flask. The mixture is first stirred 4 hours at 0° C. and then 18 hours at ambient. The product mixture is then washed twice with saturated sodium bicarbonate and the organic layer dried over sodium carbonate, concentrated by rotary evaporation and further stripped under vacuum at 60° C. (0.1 mmHg) in the presence of potassium carbonate to yield a liquid.

Example 2(i)

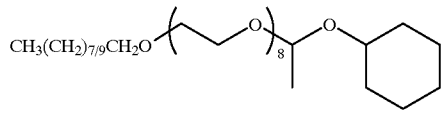

Preparation of $C_{9/11}H_{19/23}O(C_2H_4O)_8$-cyclohexyl Acetal

Neodol 91-8 (20.00 g, 39.1 mmol) is placed into a 250 ml three-necked round-bottomed flask, fitted with a heating mantle, magnetic stirrer, internal thermometer and argon inlet and dried under vacuum at 75° C. After cooling to ambient, cyclohexyl vinyl ether (5.04 g, 39.9 mmol) is added. p-Toluenesulfonic acid monohydrate (0.112 g, 0.59 mmol) is added to the mixture and stirred to dissolve. An exotherm is observed starting from 22° C. and ending at 30° C., with the development of a precipitate. After 16 minutes of reaction time, the reaction pH is adjusted to >7 with triethanolamine, filtered and then stripped in a Kugelrohr oven (50° C., 0.1 mm Hg) to yield a quantitative amount of a near colorless liquid.

Example 2(j)

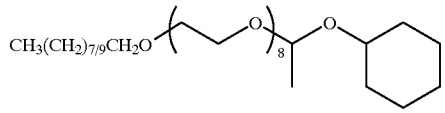

Preparation of $C_{9/11}H_{19/23}O(C_2H_4O)_8$-cyclohexyl Acetal

Neodol 91-8 (900.0 g, 1.76 mol) is placed into a 3 L three-necked rounded bottomed flask, fitted with a heating mantel, mechanical stirrer, internal thermometer, and vacuum/argon take-off adapter. The contents are dried under vacuum at 80° C. for 30 min. A portion of the dry Neodol 91-8 (20 g) is set aside after the contents are cooled to room temperature. Cyclohexylvinyl ether (217.82 g, 1.73 mol) is then added to the reaction mixture. The reagents are cooled to about 10° C. at which point methanesulfonic acid (1.80 mL) and the 20 g portion of Neodol set aside are combined and added to the reaction mixture via syringe, subsurface, in one portion. The reaction mixture exotherms, ice bath controlled, to 22° C. After 1 hour, the mixture is quenched with 15% sodium carbonate solution (35 mL). The mixture is placed under vacuum by stripping in a Kugelrohr oven (25° C., 0.1 mm Hg) for 10 min. The product is filtered to yield a quantitative amount of a near colorless liquid.

Example 3

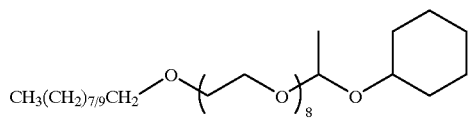

Preparation of $C_{9/11}H_{19/23}O(C_2H_4O)_8$-cyclohexyl Acetal

The procedure of Example 2 is repeated with the substitution of Neodol 91-8 for Neodol 1-7.

Example 4

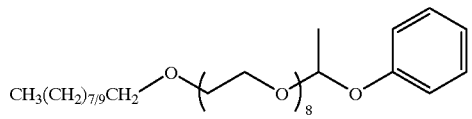

Preparation of $C_{9/11}H_{19/23}O(C_2H_4O)_8$-phenyl Acetal

The procedure of Example 3 is repeated with the substitution of phenyl vinyl ether for tert-pentyl vinyl ether.

Example 5

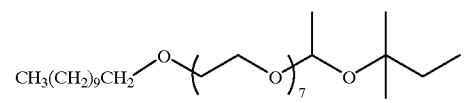

Preparation of $C_{11}H_{23}O(C_2H_4O)_7$-tert-amyl Acetal
Neodol 1-7 (20.00 g, 41.6 mmol) is placed into a 1000 ml three-necked round-bottomed flask, fitted with a heating mantle, magnetic stirrer, internal thermometer and argon inlet and dried under vacuum at 75° C. After cooling to ambient and releasing the vacuum with argon, methylene chloride (200 ml), tert-pentyl vinyl ether (14.24 g, 124.7 mmol) are added. The mixture is cooled to 0° C. and pyridinium p-toluenesulfonate (0.42 g, 1.7 mmol) is added. The mixture is first stirred 4 hours at 0° C. and then 18 hours at ambient. After diluting with diethyl ether (200 ml), the mixture is washed twice with saturated sodium bicarbonate and the organic layer dried with sodium sulfate/potassium carbonate. The product was concentrated by rotary evaporation and dried under vacuum in the presence of potassium carbonate to yield a nearly colorless liquid.

Example 6

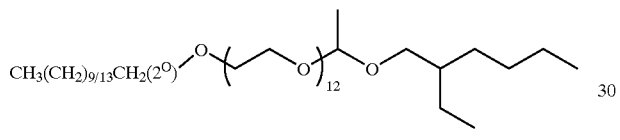

Preparation of $C_{11/15}H_{23/31}O(C_2H_4O)_{12}$-2-ethylhexyl Acetal
The procedure of Example 2 is repeated with the substitution of 2-ethylhexyl vinyl ether for cyclohexyl vinyl ether and Tergitol-15-S-12 for Neodol 1-7.

Example 7

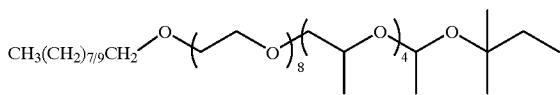

Preparation of $C_{9/11}H_{19/23}O(C_2H_4O)_8(C_3H_6O)_4$-tert-amyl Acetal
The procedure of Example 1 is repeated with the substitution of propylene oxide for 1,2 epoxybutane, tert-amyl vinyl ether for 2-ethylhexyl vinyl ether, and Neodol 91-8 for Neodol 1-7.

Example 8

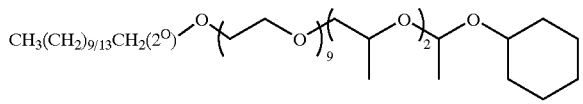

Preparation $C_{11/15}H_{23/31}O(C_2H_4O)_9(C_3H_6O)_2$-cyclohexyl Acetal
The procedure of Example 1 is repeated with the substitution of propylene oxide for 1,2-epoxybutane, cyclohexyl vinyl ether for 2-ethylhexyl vinyl ether, and Tergitol 15-S-9 for Neodol 1-7.

Example 9

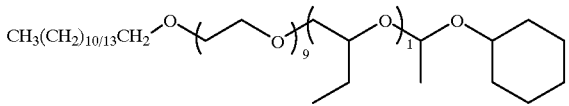

Preparation of $C_{12/15}H_{25/31}O(C_2H_4O)_9(C_4H_8O)$-cyclohexyl acetal
The procedure of Example 1 is repeated with the substitution of cyclohexyl vinyl ether for 2-ethylhexyl vinyl ether and Neodol 25-9 for Neodol 1-7.

Example 10

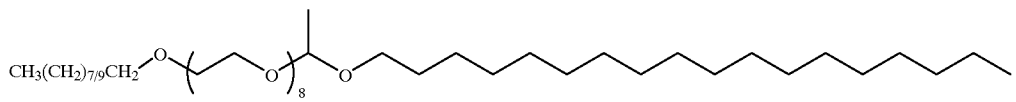

Preparation of $C_{9/11}H_{19/23}O(C_2H_4O)_8$-octadecyl Acetal
The procedure of Example 2 is repeated with the substitution of octadecyl vinyl ether for cyclohexyl vinyl ether and Neodol 91-8 for Neodol 1-7.

Example 11

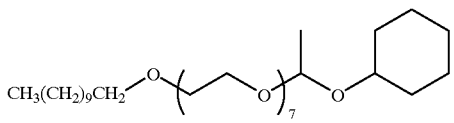

Preparation of $C_{11}H_{23}O(C_2H_4O)_7$-cyclohexyl Acetal
Neodol 1-7 (50.00 g, 104.0 mmol) is placed into a 1000 ml three-necked round-bottomed flask, fitted with a heating mantle, magnetic stirrer, internal thermometer and argon inlet and dried under vacuum at 75° C. After cooling to ambient and releasing the vacuum with argon, methylene chloride (500 ml) and cyclohexyl vinyl ether (6.55g, 51.9 mmol) are added. The mixture is cooled to 0° C. and pyridinium p-toluenesulfonate (1.04 g, 4.2 mmol) is introduced into the flask. The mixture is first stirred 4 hours at 0° C. and then 18 hours at ambient. The product mixture is then washed twice with saturated sodium bicarbonate and the organic layer dried with magnesium sulfate, concentrated by rotary evaporation and further stripped under vacuum at 60° C. (0.1 mmHg) to yield a redibrown liquid. Example 12

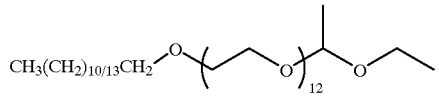

Preparation of $C_{12/15}H_{25/31}O(C_2H_4O)_{12}$-ethyl Acetal
Neodol 25-12 (76.61 g, 104.0 mmol) is placed into a 1000 ml three-necked round-bottomed flask, fitted with a heating mantle, magnetic stirrer, internal thermometer and argon inlet and dried under vacuum at 75° C. After cooling to ambient and releasing the vacuum with argon, methylene chloride (500 ml) and ethyl vinyl ether (7.50, 104.0 mmol) are added. The mixture is cooled to 0° C. and pyridinium p-toluenesulfonate (1.04 g, 4.2 mmol) is introduced into the flask. The mixture is first stirred 4 hours at 0° C. and then 18 hours at ambient. The product mixture is then washed twice with saturated sodium bicarbonate and the organic layer dried with magnesium sulfate, concentrated by rotary evaporation and further stripped under vacuum at 60° C. (0.1 mmHg) to yield a red/brown liquid.

Example 13

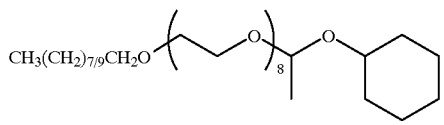

Preparation of $C_{9/11}H_{19/23}O(C_2H_4O)_8$-cyclohexyl Acetal

Neodol 91-8 (100.0 g, 195.7 mmol) is placed into a 250 ml three-necked rounded bottomed flask, fitted with a heating mantel, magnetic stirrer, internal thermometer, and vacuum/argon take-off adapter. The contents are dried under vacuum at 80° C. After cooling to ambient, methanesulfonic acid (0.28 g, 2.9 mmol) is added. Cyclohexylvinyl ether (25.19 g, 199.6 mmol) is then added dropwise to the reaction mixture over 30 minutes with an observed exotherm to about 40° C. Five minutes after the completion of the addition of the cyclohexyl vinyl ether, the reaction pH is adjusted to $\geq 7$ with triethanolamine, filtered and then stripped in a Kugelrohr oven (50° C., 0.1 mm Hg) to yield a quantitative amount of a near colorless liquid.

Example 14

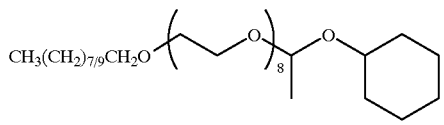

Preparation of $C_{9/11}H_{19/23}O(C_2H_4O)_8$-cyclohexyl Acetal

Anhydrous Neodol 91-8 (18.21 g, 35.6 mmol) is blended with cyclohexyl vinyl ether (12.10 g, 95.9 mmol) and placed into a 30 ml gas tight syringe. Methanesulfonic acid (0.14 g, 1.5 mmol) is blended with anhydrous Neodol 91-8 (31.79 g, 62.2 mmol) and placed into a 30 ml gas tight syringe. The syringes are loaded into a syringe pump. The contents of the syringes (at ambient) are added simultaneously at an equal rate to a 250 ml three-necked round-bottomed flask, equipped with a magnetic stirrer, internal thermometer and argon inlet. Total addition time is 60 minutes and an exotherm to 30° C. is observed. Thirty minutes after the addition is complete, the reaction pH is adjusted to $\geq 7$ with 15% sodium carbonate. The mixture is placed under vacuum by stripping in a Kugelrohr oven (50° C., 0.1 mm Hg) for 10 min. The product is filtered to yield a quantitative amount of a near colorless liquid.

Example 15

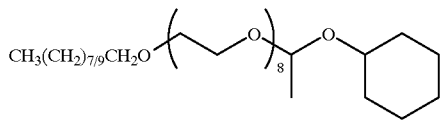

Preparation of $C_{9/11}H_{19/23}O(C_2H_4O)_8$-cyclohexyl Acetal

Cyclohexyl vinyl ether (13.0 g, 103.0 mmol) is placed into a 250 ml three-necked round-bottomed flask, fitted with a magnetic stirrer, internal thermometer and argon inlet. Methanesulfonic acid (0.14 g, 1.5 mmol) is blended with anhydrous Neodol 91-8 (50.9 g, 99.6 mmol) and placed into a 30 ml syringe. The syringe is placed into a syringe pump and the contents are added to the reaction flask over 3 hours. An exotherm to 25° C. is observed. Thirty minutes after the addition is complete, the reaction pH is adjusted to $\geq 7$ with 15% sodium carbonate. The mixture is placed under vacuum by stripping in a Kugelrohr oven (50° C., 0.1 mm Hg) for 10 min. The product is filtered to yield a quantitative amount of a yellow liquid.

Example 16

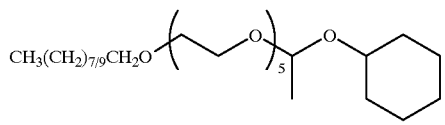

Preparation of $C_{9/11}H_{19/23}O(C_2H_4O)_5$-cyclohexyl Acetal

Neodol 91-5 (100.0 g, 263.9 mmol) is placed into a 250 ml three-necked round-bottomed flask, fitted with a heating mantel, magnetic stirrer, internal thermometer, and vacuum/argon take-off adapter. The contents are dried under vacuum at 80° C. for 10 min. A portion of the dry Neodol 91-5 (2 g) is set aside after the contents are cooled to room temperature. Cyclohexyl vinyl ether (32.97 g, 261.2 mmol) is then added to the reaction mixture. The reagents are cooled to about 15° C. at which point methanesulfonic acid (0.28 g, 2.9 mmol) and the 2 g portion of Neodol set aside are combined and added to the reaction mixture via syringe, subsurface and in one portion. The reaction mixture exotherms to 40° C. After 5 minutes, the reaction pH is adjusted to $\geq 7$ with 15% sodium carbonate. The mixture is placed under vacuum by stripping in a Kugelrohr oven (50° C., 0.1 mm Hg) for 10 min. The product is filtered to yield a quantitative amount of a near colorless liquid.

Example 17

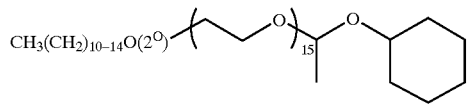

Preparation of $C_{11/15}H_{23/31}O(C_2H_4O)_{15}$-cyclohexyl Acetal

Tergitol 15-S-15 (100.0 g, 193.8 mmol) is placed into a 250 ml three-necked round-bottomed flask, fitted with a heating mantel, magnetic stirrer, internal thermometer, and vacuum/argon take-off adapter. The contents are dried under vacuum at 80° C. for 10 min. A portion of the dry Tergitol 15-S-15 (2 g) is set aside after the contents are cooled to room temperature. Cyclohexyl vinyl ether (24.21 g, 191.9 mmol) is then added to the reaction mixture. The reagents are cooled to about 15° C. at which point methanesulfonic acid (0.28 g, 2.9 mmol) and the 2 g portion of Tergitol 15-S-15 set aside are combined and added to the reaction mixture via syringe, subsurface and in one portion. The reaction mixture exotherms to 40° C. After 5 minutes, the reaction pH is adjusted to $\geq 7$ with 15% sodium carbonate. The mixture is placed under vacuum by stripping in a Kugelrohr oven (50° C., 0.1 mm Hg) for 10 min. The product is filtered to yield a quantitative amount of a near colorless liquid.

Example 18

Polymer Compositions

These compositions are useful as a backing for textiles, particularly nylon carpet which, when applied to such materials, produces a construction that exhibits lower smoke and toxic gas emissions when burned. Formula 18A contains a nonionic wetting agent herein as dispersing and foam control agent for aiding in the dispersal of polymeric carpet backing. Formula 18B contains the nonionic wetting agent only for dispersion. Each ingredient is numbered and a more detailed ingredient description as well as its function and source is given below the table.

| | | % by weight | |
|---|---|---|---|
| | Component | 18A | 18B |
| 1. | PR-240 main dispersion | 22.00 | 22.00 |
| 2. | Water | Balance | Balance |
| 3. | 2-Propanol | 4.00 | 4.00 |
| 4. | N-Methyl-2-Pyrrolidone | 1.70 | 1.70 |
| 5. | Ether capped poly(oxyalkylated) alcohol | 2.00 | 1.50 |
| 6. | Lorama ECO R1 polysaccharide resin | 7.00 | 7.00 |
| 7. | Melamine | 10.00 | 10.00 |
| 8. | FR Cros 484 Ammonium polyphosphate | 30.00 | 30.00 |
| 9. | Pentaerythritol | 10.00 | 10.00 |
| 10. | 5099 black iron oxide | 1.00 | 1.00 |
| 11. | Dow Corning Antifoam "A" | 0.00 | 0.05 |
| 12. | Aqueous dispersion of Rheox Bentone A.D. | 4.00 | 4.00 |

1. PR-240 is a solvent-free anionic aliphatic polyurethane dispersion in water. Typical resin solids are 38–42% with viscosity @ 25° C. Ford Cup of 10–50 seconds, with a specific gravity of 1.06 gm/cm$^2$ and a pH of 5–8. This is used as a binder for the nylon fibers of the carpet and to hold the other additives in place. This polyurethane dispersion exhibits low smoke and low toxicity when burned. PR-240 is a product of Bayer Industrial Chemicals.
2. Water is used as a diluent and for viscosity control. When the backcoating cures, the water evaporates and is no longer present.
3. 2-Propanol is a commodity solvent used to reduce the viscosity and adjust surface tension to help the polyurethane resin seek and bind to the nylon fibers. 2-Propanol evaporates during the curing and is not present in dried backing films.
4. N-Methyl-2-Pyrrolidone is a commodity solvent used to reduce the viscosity and adjust surface tension to help the polyurethane resin seek and bind to the nylon fibers. N-Methyl-2-Pyrrolidone evaporates during the curing and is not present in dried backing films.
5. The ether-capped poly(oxyalkylated) alcohol is the wetting agent prepared in Example 1.
6. Lorama ECO R1 polysaccharide resin is a binder resin made of natural polysaccharides. It allows use of a wider range of polyurethane dispersions as a substitute for PR-240. It adds to fire resistance, acts as an additional dispersing agent, and assists as a char former. Lorama ECO R1 is a product of Lorama Chemicals, Inc.
7. Melamine is a commodity chemical used as part of the fire retardant package. It is a spumescent that becomes gaseous when decomposed.
8. FR Cros 484 is an ammonium polyphosphate used as part of the fire retardant package. It acts as a catalyst to extinguish the flame when burned. FR Cros 484 is a product of Chemische Fabrik Budenheim.
9. Pentaerythritol is a commodity chemical used as part of the fire retardant package. It is used as a char former for flame extinguishing.
10. 5099 black iron oxide is used as a shading pigment. 5099 black iron oxide is a product of Harcos Chemical.
11. Dow Corning Antifoam "A" is a de-foaming product of the Dow Corning Company.
12. Premix of 4% Bentone A.D. and 96% water. Bentone A.D. is a special clay filler that, when premixed with water, produces a gel-structured material that stabilizes the system preventing settling without excessive thickening.

Example 19

Polymer Compositions

These are examples of preferred compositions using a low foaming nonionic surfactant of the invention as a wetting agent to aid in emulsifying polymeric compositions that are applied to fabrics. These compositions are excellent for flame retarding textile materials including polyester/cotton blend fabrics.

| | Component | 19A (% by weight) | 19B (% by weight) |
|---|---|---|---|
| 1. | Tetrakis(hydroxymethyl)phosphonium phosphate acetate, 65% aqueous solution | 50 | — |
| 2. | Tetrakis(hydroxymethyl)phosphonium phosphate oxylate, 65% aqueous solution | — | 50 |
| 3. | Water | 7.4 | 7.4 |
| 4. | Ether capped poly(oxyalkylated) alcohol | 0.2 | 0.2 |
| 5. | Urea | 12.4 | 12.4 |
| 6. | Emulsion Concentrate | 30 | 30 |

1) Tetrakis(hydroxymethyl)phosphonium phosphate acetate, 65% aqueous solution is a water soluble quaternary phosphonium salt.
2) Tetrakis(hydroxymethyl)phosphonium phosphate oxylate, 65% aqueous solution is a water soluble quaternary phosphonium salt.
3) Water is used to balance the formula.
4) Ether capped poly(oxyalkylated) alcohol is the wetting agent employed in Example 5.
5) Urea is a water soluble organic nitrogen containing compound.
6) Emulsion Concentrate is comprised of an 80% Tris(2,3-dibromopropyl) phosphate and 20% Emulsifying Agent-blend of phosphated and unphosphated nonionic having an acid number of about 49.1 and a phosphorus content of about 2.31 percent (AM2-10C brand emulsifying agent, Witco Chemical Company, Inc. Chicago, Ill.)

Example 20

Defoaming Composition

This is an anti-foaming solution containing a nonionic wetting agent herein for fermentation. This solution provides foam breaking and foam inhibiting effects so that it has excellent anti-foaming properties and does not adversely affect fermentation production.

Composition 20A

Medium Solution

In a fermentation medium containing 10 wt. % (in terms of sugar) of cane molasses, 0.5 wt. % of urea and 0.3 wt. % of corn steep liquor, *Cornebacterium glutamicum* is inoculated and cultured in a Sakaguchi flask at 31 .5° C. At the beginning of the logarithmic growth phase, polyoxyethylene monopalmitate is added to the medium in an amount of 0.15 wt. % followed by culturing at 33° C. for 10 hours.

Antifoam Solution

In a 500 ml measuring cylinder, a 100 ml portion of the culture solution so obtained is weighed, to which air is fed at 5 l/minute At the point when foams reach 300 ml, a 10 wt. % aqueous solution of the nonionic ether capped poly (oxyalkylated) alcohol employed in Example 15, is added in an amount of 0.01 g. This is set to aerate for 30 minutes.

Example 21

Defoaming Composition

This composition has particular use in aqueous pulp defoaming applications. The composition comprises a silicone defoaming agent which includes a silicone fluid, silica, a nonionic wetting agent herein, silicone containing surface active agents and water.

Composition 21A

In a separate vessel 1.5 parts of ether capped poly(oxyalkylated) alcohol as employed in Example 1, and 3.0 parts of sorbitan monosterate are added to 63 parts of water. The mixture is heated to 65.5° C. and mixed and held at this temperature for 30 minutes. 23 parts of polyorganosiloxane having a viscosity ranging between 50 to about 30,000 centistrokes at 25° C. is pumped into this mixture, followed by the addition of 7 parts of a silicone surfactant, dimethyl, 3 hydroxypropyl ethoxylated-propoxylated siloxane and/or silicon (CAS Registration No. 68937-55-3). The contents are mixed for 30 minutes. 3 parts of a polyacrylate dispersant (Colloid 1560, Rhodia) diluted with 50% water is added and the mixture is mixed for 30 minutes. 0.15 parts of NaOH (50% solution) is added. The mixture is agitated for 30 minutes and the vessel contents are allowed to cool to 32.2–37.8° C. 0.100 parts of a biocide that is a 20% solution of 1,2-benzisothiazolin 3:1 in dipropylene glycol is added and the entire vessel contents are mixed until homogeneous.

Example 22

Biocides

These compositions are aqueous concentrated plant treatment formulas that are comprised of (a) a water-soluble exogenous chemical (b) an aqueous dilutent (c) one or more nonionic surfactants and (d) an amount of a solid inorganic particulate colloidal material to stabilize the composition.

| Components | 22A (Aqueous composition) | 22B (Aqueous composition) | 22C (Dry composition) | 22D (Dry composition) |
| --- | --- | --- | --- | --- |
| 1) Glyphosphate | 480 g a.e./l | 480 g a.e./l | 65 a.e. | 65 a.e. |
| Items below on % w/w basis: | | | | |
| 2) Bu Stearate | 1.0% | — | — | — |
| 3) Ether capped poly(oxyalkylated) alcohol | 10% | 6.0% | 12.5% | 25% |
| 4) Aerosil 380 | 1.3% | 1.5% | 1.0% | 1.0% |
| 5) Steareth-20 | — | — | 12.5% | — |

1) Glyphosphate is the soluble exogenous chemical.
2) Bu Stearate is a fatty acid ester.
3) Ether capped poly(oxyalkylated) alcohol is the nonionic wetting agent from Example 15.
4) Aerosil 380 is made by Degussa, and is an amorphous silica, 380 m$^2$/g.
5) Steareth-20 is a fatty alcohol ethoxylate surfactant, i.e. Brij 78 (ICI).

Example 23

Biocides

These compositions are aqueous solutions of surfactants and low-foam concentrated liquid preparations of plant protection agents. The formulas are comprised of 1) an herbicidal active or exogenous chemical, 2) an anionic wetting agent 3) one or more nonionic wetting agents having antifoaming characteristics and 4) water.

| Components | 23A % by weight | 23B % by weight | 23C % by weight |
| --- | --- | --- | --- |
| 1) Glufosinate-ammonium | 18 | 18 | 18 |
| 2) Na (C12–C16) alcohol polyglycol ether sulfate (70% strength in water) | 30 | 30 | 30 |
| 3) Propylene glycol monomethyl ether. | 10 | 10 | 10 |
| 4) Ether capped poly(oxyalkylated) alcohol | 0.25 | 1.0 | 2.5 |
| 5) Water | Balance | Balance | Balance |

Components 1, 2, 3, and 5 are mixed at 40° C. until a clear solution is formed, after which Component 4 is added.
1) Glufosinate-ammonium is the soluble exogenous chemical.
2) Na (C12–C16) alcohol polyglycol ether sulfate (70% strength in water) is an anionic wetting agent.
3) Propylene glycol monomethyl ether is a nonionic surfactant from the polyglycol series.
4) Ether capped poly(oxyalkylated) alcohol is the nonionic, defoaming wetting agent in Example 7.
5) Water is used for the balance of the formula.

Example 24

Biocides

These are pesticidal compositions in aqueous suspoemulsions, comprising at least 2 pesticides which are insoluble in water, where one is a solid and the other is a liquid or dissolved in organic solvent, and a combination of surfactants comprising 1) a nonionic, low foaming wetting agent herein, 2) a tristyrylphenol-ethoxylate having 14–18 mol ethoxylate in form of sulfate or phosphate, in anionic or acid form, and 3) a dialkylsulfosuccinate salt.

| Components | 24A % by weight | 24B % by weight | 24C % by weight |
| --- | --- | --- | --- |
| 1) Atrazine | 31 | 31 | 31 |
| 2) Metolachlor | 21 | 21 | 21 |
| 3) Ether capped poly(oxyalkylated) alcohol | 4.6 | 1.5 | 2.5 |
| 4) Soprophor 4D384 | 1.2 | 2 | 2.5 |
| 5) Geropon DOS/PG | 1.2 | 4 | 3 |
| 6) 1,2 Propylene glycol | 5 | 5 | 2 |
| 7) Rhodorsil 426 | 0.3 | 0.3 | 0.3 |
| 8) Proxel BD | 0.12 | 0.12 | 0.12 |
| 9) Rhodopol 23 | 0.12 | 0.12 | 0.12 |
| 10) Water | Balance to 100 | Balance to 100 | Balance to 100 |

1) Atrazine is the solid form herbicide insoluble in water.
2) Metolachlor is a liquid form herbicide dissolved in a hydrophobic organic solvent.
3) Ether capped poly(oxyalkylated) alcohol is the nonionic, low foaming wetting agent employed in Example 14.
4) Soprophor 4D384 (Rhodia) is an anionic surfactant. The chemical name is Tristyrylphenol-16 EO, ammonium sulfate.
5) Geropon DOS/PG (Rhodia) is a dialkyl-sulfosuccinate salt. The chemical name is sodium dioctyl sulfosuccinate (65% in propyleneglycol).
6) 1,2 Propylene glycol is used as an antifreezer.
7) Rhodorsil 426 (Rhodia) is a polymethysiloxan defoaming agent.
8) Proxel BD (ICI) is the preservative/biocide sodium 1,2 benzisothiazol-3 (2H)-one.
9) Rhodopol 23 (Rhodia) is a heteropolysaccharide thickener.
10) Water is used as balance.

Example 25

Coating Composition

The composition is comprised of a polyol, a nonionic wetting agent herein, a halogenated polyolefinic resin material or other similar halogenated resin such as PVC, an aliphatic amine and water. This formula is suitable for coating a variety of substrates including polyolefinic substrates such as polypropylene and operates without aromatic organic solvents.

Composition 25A (1) Ethylene Glycol in the amount of 110 g is admixed with 17 g of (2) ether capped poly(oxyalkylated) alcohol employed from Example 13. The admixture is heated to 98.9° C. under agitation. 67.5 g of (3) CPO-343-1 (100%) is mixed in until it melts and disperses. The temperature is maintained at about 98.9° C. for about 10 minutes. At that time, 2.1 g of (4) amine is added. The mixture is mixed for three to five minutes to increase temperature to 115.5–121.1° C. A hot water supply is heated to 60° C. and is maintained at that temperature throughout several water additions. 20 g of the hot water is added to the admixture at a slow rate. As the hot water becomes absorbed into the molten mass, agitation is increased. Upon absorption of the hot water, 20 additional g of hot water is slowly added to the molten mass. Temperature is maintained at about 93.3–98.9° C. Agitation is increased and 1970 g of hot water, from the hot water supply, is added to the admixture.

1) Ethylene Glycol is the polyol.
2) Ether capped poly(oxyalkylated) alcohol as employed in Example 13.
3) CPO-343-1 (100%) is a chlorinated polyolefinic resin.
4) The amine is 2-amino-2-methyl-1propanol (AMP95™).

Example 26

Latex Compositions

Compositions for suppressing dust on dirt or gravel roads can comprise 0.1-35 parts by weight of a water-soluble lignosulfonate anionic surfactant, 0.1-35 parts by weight of one or more nonionic surfactants, 5-85 parts by weight of petroleum resin and 1-99 parts water. Examples of such compositions follow.

| Components | 26A % by weight | 26B % by weight | 26C % by weight |
|---|---|---|---|
| 1) Norlig TSFL | 22% | — | — |
| 2) Norlig A | — | 22% | 27% |
| 3) Ether capped poly(oxyalkylated) alcohol | 3% | 3% | 2.7% |
| 4) Triton N-57 | — | — | 0.3% |
| 5) 2600 Vis Resin | 41% | 41% | 50% |
| 6) Water | 34% | 34% | 20% |

1) Norlig TSFL is the trade name of a commercially available ammonium lignosulfate.
2) Norlig A is the trade name of a commercially available calcium lignosulfate.
3) Ether capped poly(oxyalkylated) alcohol is the nonionic wetting agent employed in Example 15.
4) Triton N-57 is a nonionic polyethoxylated alkylphenol.
5) 2600 Vis Resin is a petroleum resin sold commercially by Pennzoil Products Company.
6) Water is used for balance.

Example 27

Car Cleaning/Coating Compositions

These are cleaning and protectant compositions for automotive painted surfaces that includes a low foaming nonionic surfactant, a silicone antifoam emulsion and a volatile silicone fluid.

| Component | 27A % by weight | 27B % by weight | 27C % by weight |
|---|---|---|---|
| 1) Water | 31.55 | 38.10 | 32.10 |
| 2) Titanium Dioxide | 0.15 | — | — |
| 3) Xanthan Gum | 0.40 | 0.40 | 0.40 |
| 4) Cocamide DEA | 2.00 | — | 2.00 |
| 5) Neodol 1-7 | 2.00 | — | — |
| 6) SLES | 2.00 | — | — |
| 7) Ether capped poly(oxyalkylated) alcohol | 3.00 | 3.00 | 3.00 |
| 8) Amine Oxide | — | — | 2.00 |
| 9) ALES | — | — | 2.00 |
| 10) Volatile Silicone | 15.00 | 15.00 | 15.00 |
| 11) 10,000 cSt. Silicone Fluid | 12.00 | 12.0 | 12.0 |
| 12) 350 cSt. Silicone Fluid | 22.00 | 22.00 | 22.00 |
| 13) 50 cSt. Silicone Fluid | 3.00 | 3.00 | 3.00 |
| 14) Masil 124 Amino Functional Silicone | 1.00 | 1.00 | 1.00 |
| 15) Silicone Antifoam Emulsion | 5.00 | 5.00 | 5.00 |
| 16) Fluoro Surfactant | 0.40 | — | — |
| 17) Fragrance | 0.50 | 0.50 | 0.50 |

1) Water is for balance.
2) Titanium Dioxide is a preferred filler.
3) Xanthan Gum is a preferred thickener.
4) Cocamide DEA is a preferred fatty acid amide.
5) Neodol 1-7 is a nonionic detergent surfactant to aid in cleaning or protecting properties.
6) SLES is an anionic detergent surfactant to aid in cleaning or protecting properties.
7) Ether capped poly(oxyalkylated) alcohol is the low foaming nonionic wetting agent as employed in Example 11.
8) Amine Oxide is a surfactant used for cleaning or protecting properties.
9) ALES is an anionic detergent surfactant to aid in cleaning or protecting properties.
10) Volatile Silicone is a polydimethylcyclosiloxane that promotes leveling of the residual silicone polish film.
11) 10,000 cSt. Nonvolatile Silicone Fluid is a preferred organopolysiloxanes that provides protective film on the surface that exhibits high gloss, improved color brilliance and water beading.
12) 350 cSt. Nonvolatile Silicone Fluid is a preferred organopolysiloxanes that provides protective film on the surface that exhibits high gloss, improved color brilliance and water beading.
13) 50 cSt. Nonvolatile Silicone Fluid is a preferred organopolysiloxanes that provides protective film on the surface that exhibits high gloss, improved color brilliance and water beading.
14) Masil 124 is an amino-functional silicone manufactured by PPG Mazer Chemicals.
15) Silicone Antifoam Emulsion is sold by Osi Specialites under the trade name Sag 10, a proprietary silicone antifoam agent emulsified in water.
16) Fluoro surfactant is an anionic surfactant used for cleaning or protecting properties.
17) Fragrance is an optional ingredient.

Example 28

Coatings

These are non-foaming, water based aerosol paint compositions that avoid the use of organic solvents and are capable of providing a high gloss pigmented finish. They comprise a propellant and a water based concentrate that essentially contains water, a film forming acrylic polymer and a lower aliphatic monohydric alcohol. Composition 28A contains the ether capped poly(oxyalkylated) alcohol to aid in suspending the black pigment in the liquid vehicle. In Composition 28B the ether capped poly(oxyalkylated) alcohol is used as both a suspending agent and a defoamer.

| Components | 28A (% by weight) | 28B (% by weight) |
|---|---|---|
| 1) Propellant | 25.00 | 25.00 |
| 2) W.L. 91 Emulsion | 32.10 | 32.10 |
| 3) Water | 7.24 | 7.04 |
| 4) Isopropanol (98%) | 24.19 | 24.19 |
| 5) Black pigment | 4.45 | 4.45 |
| 6) Ether capped poly(oxyalkylated) alcohol | 0.54 | 1.00 |
| 7) Butyl Cellosolve | 4.92 | 4.92 |
| 8) BYK 301 | 0.10 | 0.10 |
| 9) L 475 | 0.26 | — |
| 10) 5% Solution ammonia | 0.22 | 0.22 |
| 11) Dibutyl phthalate | 0.98 | 0.98 |

1) Propellant is a fluorocarbon propellant and can be either Freon 12 or Freon 114.
2) W.L. 91 Emulsion is a Rhom and Haas styrene-can-acrylate emulsion containing about 58% water and about 5% surfactant.
3) Water is used for balance.
4) Isopropanol is a preferred lower aliphatic monohydric alcohol.
5) Black pigment is used to pigment the film formed on the substrate.
6) Ether capped poly(oxyalkylated) alcohol is as described in Example 17.
7) Butyl Cellosolve (Trademark) is a coalescing solvent.
8) BYK 301 is a silicone resin based leveling agent.
9) L 475 is a Dow Chemical anti-foam agent.
10) 5% Solution ammonia is used as a pH stabilizer.
11) Dibutyl phthalate is a plasticizer.

Example 29

Cement

The nonionic wetting agent herein can be used as part of a cement admixture along with a sulfonated organocyclic material to provide dry shrinkage inhibition while attaining very high slump (ability to dramatically reduce the water to cement ratio) and/ or increased compressive strength.

Composition 29

A Concrete mix is formulated with a mix design of the fine aggregate equal to 665 Kg/m$^3$ West Sand, 924 Kg/m$^3$ Wrentham Crushed Stone (ASTM c-cc Grade 67), 258 Kg/m$^3$ of Portland Cement, and a water (or liquid additives) to cement ratio (L/C) of 0.44. The concrete mixes contain an air entraining agent (a commercial tall oil based product, Darex II, sold by W. R. Grace & Co.) in amounts to maintain the air content substantially constant. The concrete mixture is proportioned by the volumetric method according to American Concrete Institute guidelines. The cement has the following admixture incorporated within it.

Admixture:

0.4% NSF [a water reducing agent called naphthalenesulfonate-formaldehyde condensate (WRDA-19)]

1.4% Ether capped poly(oxyalkylated) alcohol as employed in Example 2f.

Example 30

Cement

An oil and gas well cementing composition has styrene/butadiene latex and a combination of nonionic and anionic surfactants for improved physical properties, such as improved fluid loss, free water, and rheological properties and provides good compressive strength. The nonionic wetting agent herein acts as a defoamer and a stabilizer within the composition.

Composition 30

To a Waring blender, approximately 327 ml of water is added. Next, about 1.66 g of ether capped poly(oxalkylated) alcohol of Example 2a is added and set to stir at low speed (1000 rpm). 1.32 g of a polyacrylic acid homopolymer with molecular weight of 4000 is added. Then, approximately 131.6 g of styrene/butadiene (2:1) latex is added. While the stirring is maintained at 4000 rpm, 860 g of cement is added. Soon thereafter, the stir speed is increased to 12,000 rpm and the composition is stirred for 35 seconds.

Example 31

Fertilizer

These compositions each comprise a water soluble fertilizer and a preferred surfactant system containing a nonionic low foaming wetting agent herein and an alkylpolyglucocide compatibilizer. The surfactant-compatibilizer blends of this invention are used to stabilize (i.e. establish single-phase solutions with no precipitate) high aqueous concentrations of water-soluble fertilizers:

Compositions 31A–31M

Five, 20-20-20- aqueous fertilizer solutions are prepared in 250 ml glass containers at 3 aqueous concentrations i.e., 25, 40, and 50 weight %. 1:1 weight ratio blends of the ether capped poly(oxalkylated) alcohol and C8-10 G1.7 alkylpolyglucoside (Agrimul PG 2067 sold by Henkel Corporation) at 5 concentrations from 0.25 to 4.0 weight % are individually prepared and added to each of the 20-20-20-fertilizer solutions as indicated.

| Compositions | 20-20-20- Fertilizer (Weight %) | Ether capped poly(oxalkylated) alcohol (as employed in Example 9) (Weight %) | Agrimul (Weight %) |
|---|---|---|---|
| 31A | 25 | 0.25 | 0.25 |
| 31B | 25 | 0.5 | 0.5 |
| 31C | 25 | 0.75 | 0.75 |
| 31D | 25 | 1.0 | 1.0 |
| 31E | 25 | 2.0 | 2.0 |
| 31F | 40 | 0.5 | 0.5 |
| 31G | 40 | 0.75 | 0.75 |
| 31H | 40 | 1.0 | 1.0 |
| 31I | 40 | 2.0 | 2.0 |
| 31J | 50 | 0.5 | 0.5 |
| 31K | 50 | 0.75 | 0.75 |
| 31L | 50 | 1.0 | 1.0 |
| 31M | 50 | 2.0 | 2.0 |

Example 32

Fertilizer

Controllably active fertilizer preparations used to improve the extraction of phosphorus for plants, and in the form of an emulsion-suspension or an emulsion, comprise by weight 30–90% mixtures containing plant nutrients, 5–50% water, 2–20% oleophilic organic substance, 1–25% low foaming nonionic wetting agent herein, and 0.1–10% acid or its mixture, salt or anhydride. A preferred composition follows.

Composition 32A

A mixture containing:

1) 28 g water
2) 25.6 g ammonium nitrate
3) 19.4 g of urea
4) 46.4 g of apatite and -continued A mixture containing:

5) 35.8 g of potassium sulfate
   is ground by a ball mill. Then
6) 12.3 g of rapeseed oil and
7) 12.3 g ether capped poly(oxalkylated) alcohol
   are added to the resulting suspension, and the mixture is
   emulsified with a rod mixer. Finally
8) 12.6 g of nitric acid is added. The product is paste-like.

1) Water is used for balance.
2) Ammonium Nitrate is a plant nutrient.
3) Urea is a plant nutrient.
4) Apatite is a cheap rock phosphate.
5) Potassium sulfate is a plant nutrient.
6) Rapeseed oil is an oleophilic organic substance to improve the assimilation of phosphorus.
7) The ether capped poly(oxalkylated) alcohol is as employed in Example 9.
8) Nitric Acid is a mineral acid component that makes apatite into a form more usable for plants.

Example 33

Pharmaceuticals

These compositions are comprised of 1) particulate terfenadine, 2) a nonionic wetting agent herein and 3) spray dried sorbital particles that are loosely packed. The particulate terfenadine is a pleasant tasting, orally administrable antihistamine containing granule, that when applied to the tongue is free of the taste of solublized terfenadine.

| Components | Comp. 33A (% by weight) | Comp. 33B (% by weight) | Comp. 33C (% by weight) |
|---|---|---|---|
| 1) Terfenadine | 1.5 | 3.0 | 6.0 |
| 2) Microncrystalline Cellulose | 3.0 | 3.0 | 3.0 |
| 3) PVP (polyvinylpyrrolidone) | 5.0 | 5.0 | 5.0 |
| 4) Ether capped poly (oxyalkylated) alcohol | 1.0 | 1.5 | 4.0 |
| 5) Sorbitol INSTANT | 30.0 | 30.0 | 30.0 |
| 6) Sucrose | 39.5 | 37.5 | — |
| 7) Maltodextrin | 20.0 | 20.0 | 15.0 |
| 8) Fructose | — | — | 37.0 |

1) Terfenadine is an antihistimine particulate
2) Microncrystalline Cellulose is a suspending agent. AVICEL ™ CL-611 is used.
3) PVP is a debittering agent to terfenadine. KOLLIDON ™ K-90 is used.
4) The ether capped poly(oxyalkylated) alcohol from Example 15 is used to disperse the particulate terfenadine.
5) Sorbitol INSTANT is a flavorant from FMC.
6) Sucrose is a flavorant.
7) Maltodextrin is a flavorant. MALTRIN ™ M500 is used.
8) Fructose is a flavorant.

Example 34

Pharmaceuticals

These are compositions where a nonionic wetting agent herein is part of a water-in-oil (w/o) microemulsion that readily converts to an oil-in-water (o/w) emulsion by the addition of aqueous fluid to the w/o microemulsion, whereby any water-soluble biologically active material in the aqueous phase is released for absorption by the body. The w/o microemulsion is particularly useful for storing proteins and the like for long periods of time at room temperature and above until they are ready for use, at which time the addition of aqueous fluid converts the microemulsion to an o/w emulsion and releases the protein.

| | 34A | | 34B | |
|---|---|---|---|---|
| Component | Tradename | Amount (uL) | Tradename | Amount (uL) |
| Oil | Captex 200 | 870 | Captex 200 | 870 |
| Ether capped poly (oxyalkylated) alcohol | | 50 | | 100 |
| | Cremophor EL | 50 | N/A | N/A |
| Water | Saline | 30 | Saline | 30 |
| Total | | 100 | | 100 |

1) Captex 200 is propylene glycol esters of capric/caprylic acids (Karlshamns Lipid Specialties, Columbus OH).
2) The ether capped poly(oxyalkylated) alcohol is as employed in Example 9.
3) Cremophor EL is a polyoxyetheleneglycreol Triricinoleate 35 DAC (BASF, Inc.)
4) Saline is 0.9 wt. % NaCl.

Example 35

Toothpastes

Dental compositions for removing tobacco stain deposits on surfaces in the oral cavity, in conjunction with a toothbrush, without physically damaging the teeth can contain abrasives, binders, thickeners, sweeteners and flavorants, humectants, nonionic ether capped poly(oxyalkylated) alcohol herein that acts as a solubilizer (1–40% by wt.), and essential oils (0.2–13% by wt.). The compositions may be prepared by adding the ingredients in the following 2-step sequence. First, all powdered components of the toothpaste, such as abrasives, gelling agents, thickening agents, therapeutic agents, sweeteners, whiteners and colors are blended together. This blending may help to avoid aggregation of the gelling agents. Next, all liquid ingredients, such as aqueous solutions, humectants, nonionic surfactants, and flavoring may be blended. The blending of the liquid and powdered ingredients may be carried out in a heavy duty mixer. Following complete swelling of the gelling agents, a homogenous paste may be formed. A preferred composition follows.

Composition 35A

| Trade or Chemical Name | % by Weight |
|---|---|
| 1) Silica xerogel | 14.0 |
| 2) Silica aerogel | 7.00 |
| 3) Sodium carboxymethylcellulose | 1.00 |
| 4) Methyl Salicylate | 0.20 |
| 5) Ether capped poly(oxyalkylated) alcohol | 2.50 |
| 6) Saccharin | 0.20 |
| 7) Sorbitol solution (70%) | 69.50 |
| 8) Dye solution (Red) | 0.50 |
| 9) Flavorant | 2.00 |
| 10) Sodium lauryl sulfate | 1.50 |

-continued

| Trade or Chemical Name | % by Weight |
|---|---|
| 11) Glycerin | 1.50 |
| 12) Germicide | 0.10 |

1) Silica xerogel is a low abrasive that helps to remove tobacco from the surface after the surfactants and essential oils have partially dissolved, dispersed or solubilized the tar.
2) Silica aerogel is an inorganic gel forming, binding or thickening ingredient.
3) Sodium carboxymethylcellulose acts as a binder, thickener or gelling agent.
4) Methyl Salicylate is the essential oil and acts as a tar solubilizer, dissolver, detacher and/or dispersant.
5) Ether capped poly(oxyalkylated) alcohol as employed in Example 17 acts as the tar solubilizer and a flavor solubilizer.
6) Saccharin is a sweetener and an optional ingredient.
7) Sorbitol solution (70%) is a humectant that provides a vehicle for abrasives, surfactants, active ingredients and retains moisture.
8) Dye solution (Red) is an optional ingredient.
9) Flavorant is optional.
10) Sodium lauryl sulfate acts as a sudsing agent and tar co-solubilizer and/or dispersion aid.
11) Glycerin is a humectant that provides a vehicle for abrasives, surfactants, and active ingredients, and retains moisture.
12) Germicide is an optional ingredient.

Example 36

Toothpaste

This is a formula for an antiplaque gel dentifrice that is visually clear and has a refractive index of about 1.41 to 1.47. It consists of a polishing agent, a water insoluble noncationic antibacterial agent, an aqueous water humectant liquid vehicle and a surfactant system (anionic sulfate and a nonionic wetting agent) that increases prophylactic action, assists in achieving thorough and complete dispersion of the dentifrice throughout the oral cavity, and renders the instant compositions more cosmetically acceptable.

Composition 36A

| Components | % by weight |
|---|---|
| 1. Glycerin | 11.50 |
| 2. Sorbitol | 33.10 |
| 3. Water | 26.00 |
| 4. Sodium carboxymethylcellulose 12M8P | 1.00 |
| 5. Sodium fluoride | 0.24 |
| 6. Sodium Saccharin | 0.30 |
| 7. Luviform F-139 | 2.00 |
| 8. Sodium hydroxide | 0.60 |
| 9. Blue Dye #1 | 0.002 |
| 10. Zeodent Precipitated Silica polishing agent | 18.00 |
| 11. Sident 22S-Silica thickener | 3.50 |
| 12. Flavor | 0.958 |
| 13. Propylene Glycol | 0.50 |
| 14. Triclosan | 0.30 |

-continued

| Components | % by weight |
|---|---|
| 15. Sodium Lauryl Sulfate | 1.50 |
| 16. Ether capped poly(oxyalkylated) alcohol | 0.50 |

1. Glycerin is 99% active and is a humectant with a refractive index of 1.473.
2. Sorbitol is 70% active and is a humectant with a refractive index of 1.457.
3. Water is used as part of the aqueous phase and has a refractive index of 1.33.
4. Sodium carboxymethylcellulose 12M8P acts as a thickener.
5. Sodium fluoride assists in preventing the acid from bacteria in the mouth from attacking the teeth by dissolving the minerals out of the dentine.
6. Sodium Saccharin is sweetener.
7. Luviform F-139 is a cross-linked linear copolymer that is a water-swellable synthetic anionic polymeric polycarboxylate. It is an antibacterial enhancing agent.
8. Sodium hydroxide is used to adjust the pH of the dentifrice.
9. Blue Dye #1 is an optional ingredient.
10. Zeodent polishing agent is a precipitated silica.
11. Sident 22S-Silica thickener
12. Flavor is an additional ingredient and could be peppermint, spearmint, wintergreen, etc.
13. Propylene Glycol is a humectant in the formula.
14. Triclosan is a halogentated diphenyl ether antibacterial agent.
15. Sodium Lauryl Sulfate is an anionic surfactant.
16. Ether capped poly(oxyalkylated) alcohol is the nonionic wetting agent employed in Example 13.

Example 37

Paper Making Additive Composition

This composition can be added to tissue papers, particularly densified tissue papers, to provide an enhanced tactile sense of softness. The biodegradable softener herein is typically applied from an aqueous dispersion or solution to at least one surface of the dry tissue paper web.

Composition 37

| Component | Weight % |
|---|---|
| Ether capped poly(oxyalkylated) alcohol | 3 |
| GLYCOMUL-S CG | 12 |
| DOW 65 Additive | 1 |
| Water | 84 |

1) Ether capped poly(oxyalkylated) alcohol as employed in Example 11 is used as a biodegradable nonionic softener.
2) GLYCOMUL-S CG is a mixed sorbitan stearate ester surfactant made by Lonza, Inc.
3) DOW 65 Additive is a silicone polymer foam suppressant.
4) Water is used for balance.

Example 38

Azeotrope

In the manufacturing of highly integrated semiconductor devices, the internal atmosphere of clean rooms may be cleaned with the use of a chemical filter. However, the adsorption of organic substances onto the surface of the substrate may not be sufficiently prevented. Under these circumstances, there has been a demand for a technology capable of effectively preventing the adsorption of organic substances onto the surface of the substrate. This invention is an electronic/ electric part used in a clean room, which contains a resin base material and additives added to the resin base material.

Composition 38A

To 100 parts by weight of polypropylene resin base material (Mitsui Toatsu Chemicals, Inc.) there are added:
1) 5 parts by weight of a lubricant (Nippon Oil Co., Ltd.). The main component of the lubricant is an aliphatic hydrocarbon having 20 or more carbon atoms.
2) 3 parts weight of a plasticizer (Daihachi Chemical Industries, Ltd.). The main component of the plasticizer is sebacic acid-2-ethylhexyl.
3) 1 part by weight of an anti-oxidizing agent (Yashitomi Pharmaceutical Industries, Ltd.). The main component of the anti-oxidizing agent is stearyl-β-(3,5-di-t-butyl-4-hydroxyphenyl)propionate.
4) 2 parts by weight of an anti-electrostatic agent. The main component of the anti-electrostatic agent is an ether capped poly(oxyalkylated) alcohol as employed in Example 3.
5) 8 parts by weight of a fire retardant (Nihon Mining and Refining Co., Ltd.). The main components of the fire retardant are antimony trioxide (3 parts by weight) and paraffin chloride (5 parts by weight).

The resultant mixture is kneaded while heating. The material thus obtained is subjected to extrusion forming to prepare a box. Plates having measurements of 100 mm×100 mm and a thickness of 2 mm are cut therefrom.

Example 39

Azeotrope

Cleaning or dewatering a surface can be obtained by applying to the surface a washing composition containing a volatile methyl siloxane such as hexamethyldisiloxane or octamethyltrisiloxane, and a water displacement agent for enhancing cleaning or dewatering and comprising a nonionic wetting agent herein. While the surface is still wet with the washing composition, it is rinsed with an azeotrope containing hexamethyldisiloxane or octamethyltrisiloxane and 2-pentanol, 2-methyl-1-pentanol, 3-methyl-3-pentanol, 1-methoxy-2-propanol, 1-butoxy-2-propanol, 1-hexanol, n-propoxypopanol or ethyl lactate. The surface is then permitted to dry.

Two or more water displacement agents can also be employed in the above composition, for example as dilute solutions of a nonionic wetting agent in a volatile methyl silicone. One nonionic surfactant can be a siloxane surfactant acetoxyterminated silicone glycol "SILSUR", and the other surfactant can be the ether capped poly(oxyalkylated) alcohol employed in Example 2i. The rinse agents used to remove the non-volatile additive is either a volatile methyl siloxane alone or an azeotrope containing a volatile methyl siloxane and an alcohol. The water displacement agents and the rinse agents are immiscible and less dense than water.

Example 40

Drilling Mud Composition

This is an antifoaming composition for drilling fluids used in the drilling of subterranean wells. This composition contains a nonionic wetting agent herein, a polypropylene glycol, carbon black and an ester alcohol, and will reduce foam formation in the bore hole into the earth.

Composition 40

An antifoaming composition for drilling fluids comprises 50% by weight of the ether-capped poly(oxyalkylated) alcohol surfactant of Example 15. The surfactant is mixed with a polypropylene glycol from Dow Chemical sold under the trade name of polyol PM in an amount of 18% by weight of the antifoaming composition. The surfactant and the polypropylene glycol are combined by mixing one with the other in a high-speed dispenser and shear pump until smooth and consistent. A high speed mechanical disperser suitable in this regard comprises a device called ROTOSTAT® 20OXP-200 sold by ADMIX, Inc. The mixing is for 30 minutes. Afterwards, carbon black is added to the foregoing mixture in an amount from about 1 to about 10 weight percent of the antifoaming composition. The carbon black is Grade N-220, N-660 or N-330. The carbon black is stirred into the mixture of the surfactant and the polypropylene glycol for 1 hour, followed by the addition of 22% by weight of the compositon of an ester alcohol comprising 2,2,4-trimethyl-1,3-pentanediol monoisobutyrate, stirred in until the mixture is homogeneous. The ester alcohol is a mixture comprising about 50% to about 79% by weight of 2,2,4-trimethyl-1,3-pentanediol monoisobutyrate, about 14 to 32% by weight of 2,2,4-trimethyl-1,3-pentanediol diisobutyrate, and the balance pentanediol.

Example 41

Drilling Mud Composition

A fluid for use in drilling and completion operations can be made by mixing a salt of an alkaline earth metal with a nonionic wetting agent herein in an amount and under conditions sufficient to convert a majority of the nonionic wetting agent into water-insoluble, hydrated colloidal complexes comprising hydrated ions of alkaline earth metal complexed with the nonionic wetting agent. The complexes improve the rheology and/or fluid loss control of the fluid.

Composition 41

One laboratory barrel (350 ml) of a 1.5 kg/l brine is prepared by mixing 3 volume % (10.5 ml) of the ether capped poly(oxyalkylated) alcohol employed in Example 2h, into a 1.5 kg/l $CaCl_2$/$CaBr_2$ brine and hand shaking the mixture to simulate poor mixing conditions. The result is a milky or clouded dispersion. In order to determine whether the dispersion has elastic properties sufficient to suspend solids, 23 Kg/barrel of brine of calcium carbonate (specific gravity 2.65) is added, the mixture is hand shaken and then allowed to sit for 16 hours. The dispersion is then tested for static settling of the calcium carbonate. No settling occurs, indicating that the dispersion has desired solids suspending or elastic properties for a drilling fluid without the need to add biopolymers. Rheometer readings indicate that the fluid has an elastic structure dominating the viscous structure, confirming that the dispersion is capable of suspending particles.

Example 42

Contact Lens Cleaning Composition

A composition for cleaning and disinfecting contact lenses can comprise a carbonate or bicarbonate salt, a non-carbonate buffer system, an antimicrobial agent, and a nonionic wetting agent herein. This composition provides disinfection and cleaning of contact lenses including the prevention or removal of protein and lipid deposits and other debris.

Composition 42

| Components | Weight % |
|---|---|
| 1. Polyhexamethylene biguanide HCl | 0.00008 |
| 2. Alexidine | 0.0002 |
| 3. Boric acid | 0.83 |
| 4. Sodium phosphate (dibasic) | 0.310 |
| 5. Sodium chloride | 0.375 |
| 6. Ether capped poly(oxyalkylated) alcohol | 1.00 |
| 7. Tetrasodium phosphonate | 0.100 |
| 8. Sodium carbonate | 0.100 |
| 9. Sodium hydroxide, 1N and/or hydrochloric acid | pH adjustment |
| 10. Purified water | Balance to 100 |

1. Polyhexamethylene biguanide HCl is a disinfecting agent. When used with borate, its efficacy is enhanced. A 20% w/w solution of Cosmocil CQ from ICI, Chemicals is used.
2. Alexidine is a disinfecting agent. When used with borate its efficacy is enhanced.
3. Boric acid is a weak acid buffer.
4. Sodium phosphate (dibasic) is a weak acid buffer.
5. Sodium chloride is used as a tonicity agent to approximate the osmotic pressure of normal lacrimal fluids.
6. Ether capped poly(oxyalkylated) alcohol is the nonionic wetting agent employed in Example 8.
7. Tetrasodium phosphonate is a weak acid buffer. A 30% w/w solution available as DeQuest 2016 from Monsanto Co. is used.
8. Sodium carbonate is a preferred carbonate buffer for this formula.
9. Sodium hydroxide, 1N and/or hydrochloric acid are non-carbonate buffering components used to adjust the pH.
10. Purified water is used for balance.

The solution is prepared by gradually heating 80% of the water to 80° C. while dissolving the phosphonate and the buffer substances. The sodium chloride and carbonate are then added to the solution and dissolved, followed by the addition of surfactant. After the solution is cooled to room temperature, the alexidine and the Cosmocil CQ solutions are added through a sterile filter, followed by the balance of the Cosmocil CQ. The pH of the resting solution is about 7.3 to 7.5.

What is claimed is:

1. A wetting composition comprising:
   (a) from about 0.01% to about 50% by weight of the composition of a wetting agent, wherein said wetting agent comprises an ether-capped poly(oxyalkylated) alcohol having the formula:

$RO(R^1O)_x CH(CH_3)OR^2$ wherein R is selected from the group consisting of linear or branched, saturated or unsaturated, substituted or unsubstituted, aliphatic or aromatic hydrocarbon radicals having from about 1 to about 30 carbon atoms; $R^1$ may be the same or different, and is independently selected from the group consisting of branched or linear $C_2$ to $C_7$ alkylene in any given molecule; x is a number from 1 to about 30; and $R^2$ is selected from the group consisting of:
   (i) a 4 to 8 membered substituted, or unsubstituted heterocyclic ring containing from 1 to 3 hetero atoms;
   (ii) substituted or unsubstituted, unsaturated cyclic or aromatic hydrocarbon radicals having from about 4 to about 30 carbon atoms;
   (iii) a 7 to 13 membered substituted, or unsubstituted polycyclic ring; and
   (iv) a hydrocarbon of the formula:

$-(CH_2)_y-X$ 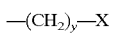

wherein y is an integer from 0 to 7, and X is a 4 to 8 membered substituted or substituted, cyclic or aromatic hydrocarbon radical; and (b) from about 0.1% to about 99% by weight of the composition of an adjunct ingredient.

2. The composition as claimed in claim 1 wherein R is a linear or branched, saturated or unsaturated, substituted or unsubstituted, aliphatic hydrocarbon radical having from about 1 to about 20 carbon atoms.

3. The composition as claimed in claim 2 wherein R is a linear or branched, saturated, aliphatic hydrocarbon radical having from about 4 to about 18 carbon atoms.

4. The composition as claimed in claim 1 wherein R has the formula:

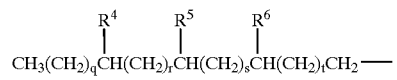

wherein $R^4$, $R^5$, and $R^6$ are each independently selected from hydrogen and $C_1$–$C_3$ alkyl, provided that $R^4$, $R^5$, and $R^6$ are not all hydrogen and, when t is 0, at least $R^4$ or $R^5$ is not hydrogen; q, r, s, and t are each independently integers from 0 to 13.

5. The composition as claimed in claim 4 wherein R has the formula:

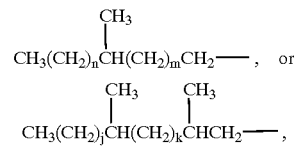

wherein n, m, j and k are each independently integers from 0 to 13.

6. The composition as claimed in claim 1 wherein $R^2$ is a 4 to 8 member substituted or unsubstituted heterocyclic ring containing from 1 to 3 heteroatoms.

7. The composition as claimed in claim 6 wherein $R^2$ is a 5 or 6 member heterocycle.

8. The composition as claimed in claim 7 wherein said heterocycle is selected from the group consisting of:

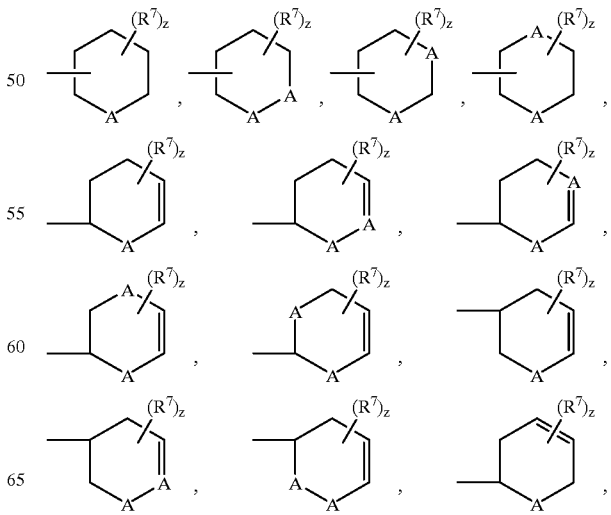

-continued

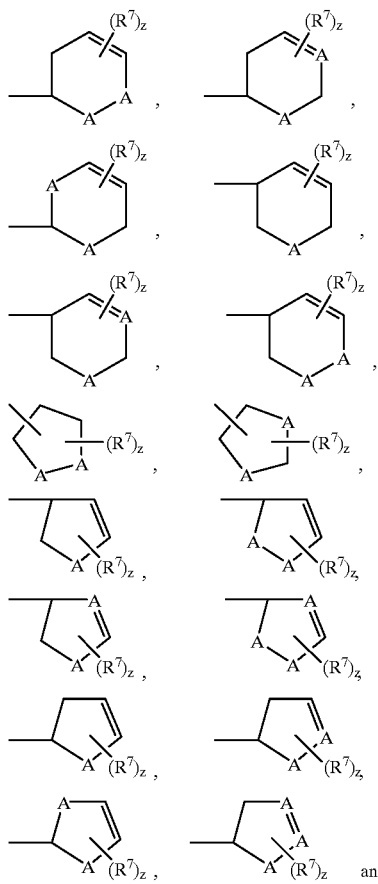

wherein each $R^7$ is independently selected from the group consisting of hydrogen and linear or branched, saturated or unsaturated, substituted or unsubstituted, aliphatic hydrocarbon or alkoxy radicals having from about 1 to about 10 carbon atoms, or $R^7$ is a saturated or unsaturated, substituted or unsubstituted, alicyclic or aromatic hydrocarbon or alkoxy radical having from about 1 to about 10 carbon atoms, which is fused to the heterocyclic ring; each A is independently selected from the group consisting of O, and $N(R^8)_a$, wherein $R^8$ is independently selected from the group consisting of hydrogen and linear or branched, saturated or unsaturated, substituted or unsubstituted, aliphatic hydrocarbon radicals having from about 1 to about 10 carbon atoms, and a is either 0 or 1; provided that any A that is bound by a double bond must be $N(R^8)_a$, wherein a=0 and z is an integer from 1 to 3.

9. The composition as claimed in claim 8 wherein said heterocycle is selected from the group consisting of:

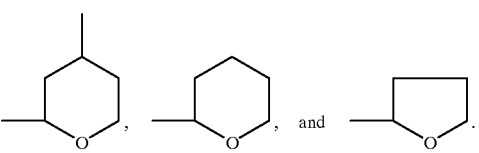

-continued

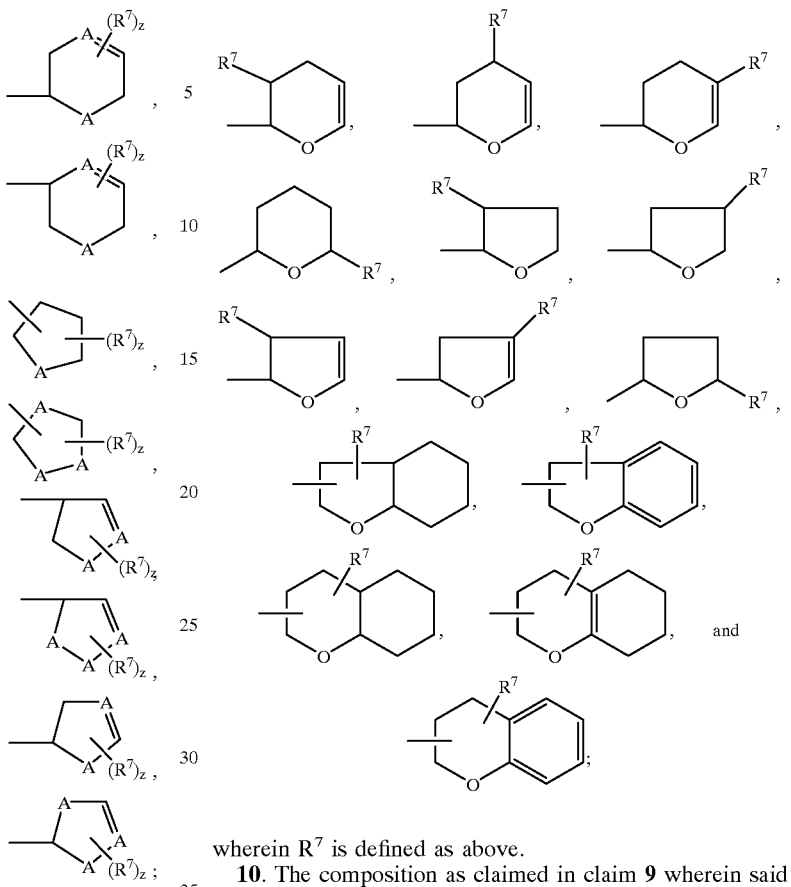

wherein $R^7$ is defined as above.

10. The composition as claimed in claim 9 wherein said ether-capped poly(oxyalkylated) alcohol contains a chiral center.

11. The composition as claimed in claim 9 wherein said heterocycle is selected from the group consisting of:

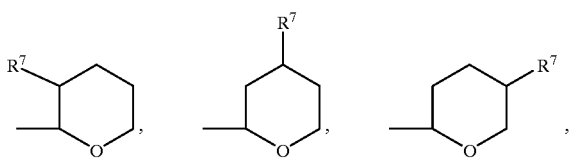

12. The composition as claimed in claim 1 wherein $R^2$ is a 7 to 13 membered substituted, or unsubstituted polycyclic ring.

13. The composition as claimed in claim 12 wherein $R^2$ is selected from the group consisting of substituted or unsubstituted adamantane, substituted or unsubstituted norbornane, substituted or unsubstituted nortricyclene, and substituted or unsubstituted bicyclo[2.2.2]octane.

14. The composition as claimed in claim 1 wherein $R^2$ is a hydrocarbon of the formula:

$$-(CH_2)_y-X$$

wherein y is an integer from 0 to 7, and X is a 4 to 8 membered substituted or unsubstituted, cyclic or aromatic hydrocarbon radical.

15. The composition as claimed in claim 14 wherein y is 0 and X is a 5 or 6 membered substituted or unsubstituted, saturated or unsaturated cyclic or aromatic hydrocarbon radical.

16. The composition as claimed in claim 15 wherein X is selected from the group consisting of:

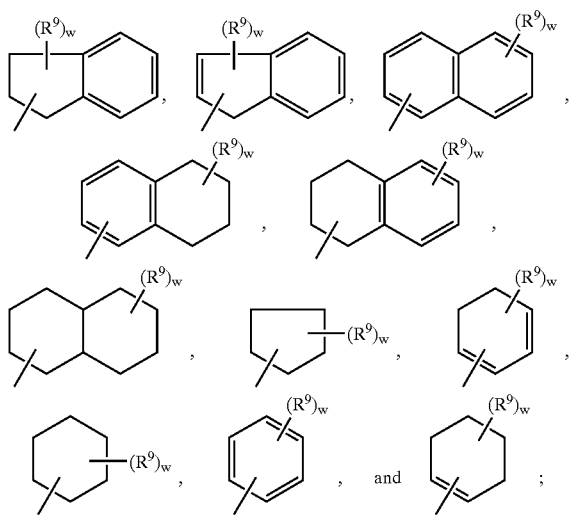

wherein each $R^9$ is independently selected from the group consisting of hydrogen, linear or branched, saturated or unsaturated, substituted or unsubstituted, aliphatic hydrocarbon or alkoxy radical having from about 1 to about 10 carbon atoms, or each $R^9$ is a saturated or unsaturated, substituted or unsubstituted, alicyclic or aromatic hydrocarbon radical having from about 1 to about 10 carbon atoms, which is fused to the ring; and w is an integer from 1 to 3.

17. The composition as claimed in claim 16 wherein X is selected from the group consisting of:

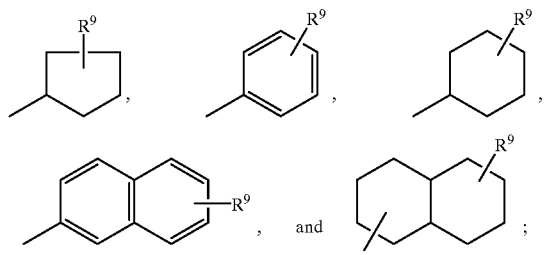

wherein $R^9$ is defined as above.

18. The composition as claimed in claim 16 wherein X is selected from the group consisting of:

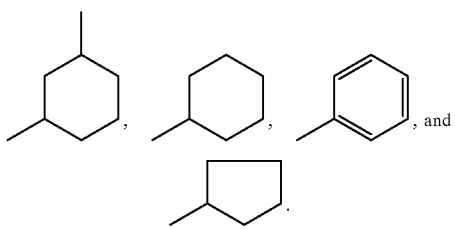

19. The composition as claimed in claim 1 wherein R is selected from the group consisting of linear or branched, aliphatic hydrocarbon radicals having from about 7 to about 11 carbon atoms; x is a number from 6 to about 10; and $R^2$ is a hydrocarbon radical of the formula:

—$(CH_2)_y$—X wherein y is 0 and X is a 5 or 6 membered substituted or unsubstituted, saturated or unsaturated, cyclic or aromatic hydrocarbon radical.

20. The composition as claimed in claim 19 wherein X is selected from the group consisting of

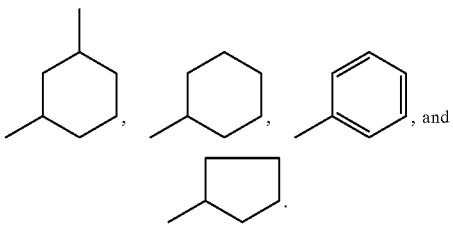

21. The composition as claimed in claim 1 wherein said composition is a polymer composition and said adjunct ingredient is selected from the group consisting of monomers, fillers, solvent, flame retardant, cross-linking agents, preservatives, pigments, catalysts, co-catalysts, anti-foaming agents, resins, viscosity control agents, wetting agents other than those of the present invention, polymers, initiators, chain transfer agents, anti-oxidants, UV absorbers and mixtures thereof.

22. The composition as claimed in claim 1 wherein said composition is a biocidal composition and said adjunct ingredient is selected from the group consisting of fillers, solvent, preservatives, pigments, anti-foaming agents, resins, viscosity control agents, wetting agents other than those of the present invention, polymers, diluents, anti-oxidants, UV absorbers, buffering agents, sticking agents, carriers, biocides, and mixtures thereof.

23. The composition as claimed in claim 1 wherein said composition is a cement and said adjunct ingredient is selected from the group consisting of aggregate, sand, water, shrinkage inhibitors, hardening accelerants, fluid loss control agents, retardants, light weight additives, heavy weight additives, binders, defoamers, solvent, wetting agents other than the wetting agents of the present invention, dyes, pigments, fillers, fluidizing agents, corrosion inhibitors, air entraining agents, polymers, and mixtures thereof.

24. The composition as claimed in claim 1 wherein said composition is a coating composition and said adjunct ingredient is selected from the group consisting of monomers, fillers, pigments, solvents, dyes, flame retardants, cross-linking agents, preservatives, pigments, catalysts, co-catalysts, anti-foaming agents, resins, viscosity control agents, wetting agents other than those of the present invention, polymers, anti-oxidants, UV absorbers, conditioning agents, biocides, fungicides, light stabilizers, anti-oxidants, reducing agents, corrosion inhibitors, carriers, rheology modifiers, propellants, plasticizers, buffers, initiators, chain transfer agents, wood preservatives, and mixtures thereof.

25. The composition as claimed in claim 1 wherein said composition is a fertilizer and said adjunct ingredient is selected from the group consisting of trace elements, binders, wetting agents other than the wetting agents of the present invention, filler, thickener, preservative, blood and bone products, ammonium nitrates, lime, sand, sources of nitrogen, buffers, nitrification inhibitors, growth hormones, antibiotics, soil-improving components, humus, peat, potassium, phosphorous, solvent, carrier, defoaming agents, micronutrients, and mixtures thereof.

26. The composition as claimed in claim 1 wherein said composition is a pharmaceutical composition and said adjunct ingredient is selected from the group consisting of medicaments, fillers, lubricants, coating agents, buffers, adhesives, gelling agents, mould release agents, flavorings, sweeteners, carriers, stabilizers, humectants, coloring agents, extenders, preservatives, wetting agents other that the wetting agents of the present invention, solvent, electrolytes, and mixtures thereof.

27. The composition as claimed in claim 1 wherein said composition is a toothpaste and said adjunct ingredient is selected from the group consisting of medicaments, dentifrices, abrasives, sources of fluorine, fillers, lubricants, coating agents, buffers, adhesives, gelling agents, polishing agents, antibacterial agents, flavorings, sweeteners, carriers, solvents, stabilizers, opacifying agents, coloring agents, extenders, preservatives, polymers, anti-calculus agents, dyes, iridescent particles, essential oil, wetting agents other that the wetting agents of the present invention, defoamers, solvent, humectants, electrolytes, binders, thickeners, rheology modifiers, and mixtures thereof.

28. The composition as claimed in claim 1 wherein said composition is a drilling fluid and said adjunct ingredient is selected from the group consisting of defoamers, solvent, wetting agents other than the wetting agents of the present invention, corrosion inhibitors, polymers, brine, viscosity agents, rehology agents, water soluble polymers, drilled solids, clay, weighting materials, gelling agents, fluid loss additives, and mixtures thereof.

* * * * *